United States Patent [19]

Eskin et al.

[11] Patent Number: 5,589,198

[45] Date of Patent: Dec. 31, 1996

[54] TREATMENT OF IODINE DEFICIENCY DISEASES

[75] Inventors: Bernard A. Eskin, 625 Harvard Rd., Bala Cynwyd, Pa. 19004; R. Alison Ghent, Kingston, Canada

[73] Assignees: 943038 Ontario, Inc., Ontario, Canada; Bernard A. Eskin, Philadelphia, Pa.

[21] Appl. No.: 388,026

[22] Filed: Feb. 13, 1995

Related U.S. Application Data

[60] Continuation-in-part of Ser. No. 131,427, Oct. 4, 1993, Pat. No. 5,389,385, which is a division of Ser. No. 803,550, Dec. 9, 1991, Pat. No. 5,250,304, which is a division of Ser. No. 292,968, Jan. 3, 1989, Pat. No. 5,171,582, which is a continuation-in-part of Ser. No. 889,947, Jul. 28, 1986, Pat. No. 4,816,255, which is a continuation-in-part of Ser. No. 760,950, Jul. 31, 1985, abandoned.

[51] Int. Cl.⁶ .......................... A01N 59/22; A61K 33/36
[52] U.S. Cl. ............................................ 424/667; 514/899
[58] Field of Search .............................. 514/899; 424/667

[56] References Cited

U.S. PATENT DOCUMENTS

| | | | |
|---|---|---|---|
| 4,816,255 | 3/1989 | Ghent et al. | 424/150 |
| 5,171,582 | 12/1992 | Ghent et al. | . |
| 5,250,304 | 10/1993 | Ghent et al. | . |
| 5,389,385 | 2/1995 | Ghent et al. | 424/667 |

OTHER PUBLICATIONS

Eskin, B. A., Thyroid Hormones and Tumor Development, Chapter 6, Influences of Hormones in Tumor Development, pp. 129–156.

Eskin, B. A. et al., "Replacement Therapy with Iodine in Breast Neoplasia," *Intl. J. of Gynec. and Obstets.*, vol. 8, p.232 (1970).

Hetzel, D. S., "Iodine Deficiency Disorders and Their Eradication," *Lancet* 12, pp. 1126–1129 (Nov. 1983).

Eskin, B. A. et al., "Human Breast Uptake of Radioactive Iodine," *Obstet. and Gynecol.*, vol. 44, No. 3, pp. 398–402 (Sep. 1985).

Honour, A. J. et al., "Secretion of Radio Iodine in Digestive Juices and Milk," in *Man Clin. Science* 11, pp. 447–462 (1952).

Kelly, F. C. et al., "Prevalance and Geographical Distribution of Indemic Goitre," *W.H.O. Monograph*, 44:27–233.

Vishnyakova, V. V. et al., "On the Treatment of Dyshormonal Hyperplasia of Mammary Glands," *Vestin. Sakad. Med. Mauk. S.S.S.R.*, 21:19 (1966).

Moosa, A. R. et al., "Thyroid Status and Breast Cancer—Royal College of Surgeons," England, 53 (1973).

Eskin, B. A., "Iodine and Breast Cancer—A 1982 Update Biological Trace Element," Research 5, pp.399–412 (1983).

Eskin, B. A. et al., "Human Breast Uptake Radioactive Iodine," *Obstet. and Gynecol.*, vol. 44, No. 3, pp. 398–402 (Sep. 1985).

Eskin, B. A., "Iodine Metabolism and Breast Cancer," *Trans. N.Y. Acad. Sciences*, Series II, vol. 32, pp. 911–947 (1970).

*Primary Examiner*—Nathan M. Nutter
*Attorney, Agent, or Firm*—Venable, Baetjer, Howard & Civiletti, LLP

[57] ABSTRACT

This invention relates to a composition for use in the treatment or prevention of iodine deficiency diseases or disorders such as fibrocystic dysplasia of the breast, breast cancer, endometriosis, ovarian cysts and premenstrual syndrome. More particularly, this invention relates to a composition for the treatment or prevention of iodine deficiency diseases or disorders, the composition comprising elemental iodine ($I_2$) which may also be referred to as metallic iodine or iodine metal. The elemental iodine can be used with any pharmaceutically acceptable carrier.

11 Claims, 13 Drawing Sheets

Breast tissue from a human female with fibrocystic disease showing epithelial hyperplasia, cystic spaces and increased fibrous tissue.

Breast tissue from a normal female rat showing a normal configuration

Breast tissue from a female rat rendered iodine deficient showing cystic spaces, epithelial hyperplasia and increased fibrous tissue.

Breast tissue from a female rat on an Iodine deficient diet with oestrogens added to the model. The cystic spaces are enhanced, the epithelial hyperplasia is more marked. The increased fibrosis between the secreting acini is also present.

Breast tissue from a female rat on a normal iodine containing diet with oestrogens added. The control rat shows some cyst formation and epithelial hyperplasia but without the fibrosis.

Breast tissue from a female rat on an iodine deficient diet with a carcinogen (Dimethyl Benzanthrene) added to the model.

Some Excess Fibrous Tissue        Some Adipose Tissue Reappearing

Breast tissue from a female rat on an iodine deficient diet and then given sodium iodide as a replacement treatment. The epithelial hyperplasia has regressed, the cystic spaces have disappeared but the fibrous tissue has remained.

Excess Fibrous Tissue

Breast tissue from a female rat on an iodine deficient diet then given Iodine Caseinate (Iodaminol, Desbergers Ltee, Montreal), as a replacement treatment. The epithelial hyperplasia has subsided, the cystic spaces are left but the fibrosis is unchanged.

Normal Adipose Tissue

Breast tissue from a female rat on iodine deficient diet then given Elemental Iodine as replacement treatment. This has returned the microscopic picture to near normal with subsidence of the epithelial hyperplasia, the cystic spaces and the fibrosis.

CHARACTERISTICS OF THE STUDY GROUP TREATED
WITH ELEMENTAL IODINE

|  | NEW PATIENTS | TRANSFER PATIENTS |
|---|---|---|
| NUMBER | 108 | 145 |
| MEAN AGE (YEARS) | 32.8 | 39.6 |
| DURATION OF SYMPTOMS (MONTHS) | 24.3 | 28.7 |
| DURATION OF TREATMENT (MONTHS) | 8.9 | 9.9 |

FIG.12

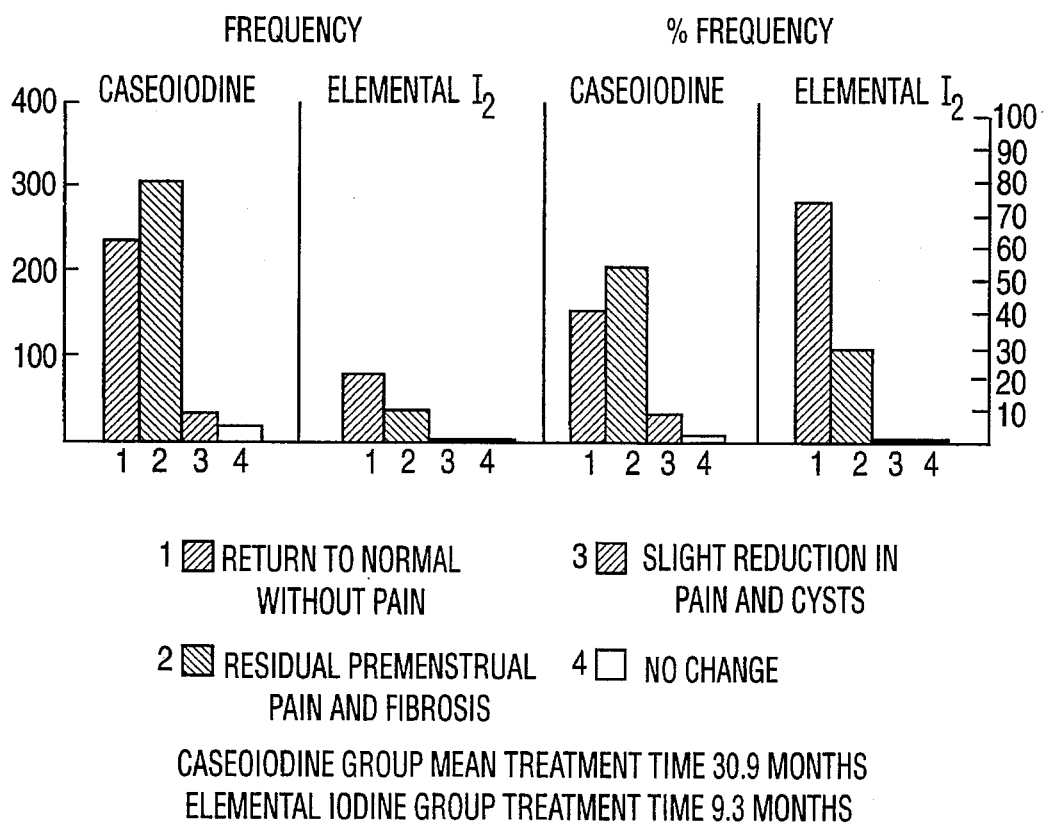

COMPARISON OF RESULTS OF REPLACEMENT THERAPY
c̄ CASEOIODINE vs ELEMENTAL IODINE (DeNOVA GROUP)

1 ▨ RETURN TO NORMAL WITHOUT PAIN
2 ▩ RESIDUAL PREMENSTRUAL PAIN AND FIBROSIS
3 ▨ SLIGHT REDUCTION IN PAIN AND CYSTS
4 ☐ NO CHANGE

CASEOIODINE GROUP MEAN TREATMENT TIME 30.9 MONTHS
ELEMENTAL IODINE GROUP TREATMENT TIME 9.3 MONTHS

FIG.13

TREATMENT OF IODINE DEFICIENCY DISEASES

CROSS-REFERENCE TO RELATED APPLICATIONS

The present patent application is a continuation-in-part application of Ser. No. 08/131,427, filed Oct. 4, 1993, now U.S. Pat. No. 5,389,385, which was a divisional application of Ser. No. 07/803,550, filed Dec. 9, 1991, now U.S. Pat. No. 5,250,304, which was a divisional application of Ser. No. 07/292,968 filed Jan. 3, 1989, now U.S. Pat. No. 5,171,582, which was a continuation-in-part application of Ser. No. 06/889,947 filed Jul. 28, 1986, now U.S. Pat. No. 4,816,255 which was a continuation-in-part application of Ser. No. 06/760,950, filed Jul. 31, 1985, now abandoned.

BACKGROUND OF THE INVENTION

The nomenclature of iodine deficiency breast syndrome has a varied past with Reclus in France, Schimmellbusch in Germany and Bloodgood in the United States contributing to the confusion. Pathological nomenclature was popular for a time with the terms fibroepitheliosis, fibroadenosis and epithelial adenosis reported in the literature. Recently, the most common name applied seems to be fibrocystic disease. It is generally agreed, that all of these terms, and several more, apply to an entity characterized by painful nodular breasts and supported pathologically with cystic spaces, epithelial hyperplasia or apocrine metaplasia and interacinar fibrosis.

The etiology of the condition has remained obscure with various theories in ascendancy at any one time. These have included a prolonged luteal phase, a reversal of the estrone/estriol ratio, increased median prolactin levels, or any upset in these complex interrelationships. All of these etiological theories are supported by good research data. More recent suggestions have implicated caffeine in coffee, tea and chocolate users and the increased estrogen intake in milk drinkers.

It is the inventors' position that there is a common denominator in all of these concepts and this is specific iodine ion deficient state. In this state, it is further postulated that the secreting cells of the breast are sensitized to various stimuli to produce the changes noted. This sensitization can progress to overt malignancy if a carcinogen is added to the rat model and possibly to the human female.

Clinically, the fibrocystic syndrome is the most common breast disease that affects North American women. The Cancer Committee of the American Academy of Pathology (1985) estimated the incidence at 50–80% of the adult female population.

Parallel findings indicate that at least fifty percent of all North American and European women of child bearing age are suffering from fibrocystic disease (fibrocystic dysplasia). Painful breasts are common prior to the onset of menstruation and fibrocystic disease accentuates this tendency. Some women suffering from this disease have hard areas of thickening with small pellet sized masses scattered throughout the breast while other patients have marble sized cyst development. Fibrocystic disease of the breast affects one in two women between the ages of 16 and 60.

The link between iodine deficiency states and an increased incidence of breast cancer is statistically valid on a geographical basis. Demographic evidence indicates that rates of morbidity and mortality due to breast cancer are higher in areas of iodine inadequacy than in regions where iodine is readily available. Demographic surveys of Japan and Iceland show low incidences of endemic non-toxic goiter and breast cancer, while Mexico and Thailand show high incidences of goiter and breast cancer. In addition, increased breast cancer in specific endemic-goiter regions in Poland, Switzerland, Australia, and the Soviet Union have been described in various publications. Similarly, in the United States and Canada iodine deficient regions (described by the World Health Organization) show a high census of breast disease.

The treatment of fibrocystic disease in the past has included neglect, hormonal manipulation with birth control pills, danazol (a masculinizing hormone), withdrawal of caffeine and cow's milk, or subcutaneous mastectomy. The treatment of this syndrome by a non-surgical technique with very low side effects would be more desirable and is offered by this invention.

Previously, iodine, a trace element in the basic physiology of humans, has received much attention in its application to thyroid function. This led, in 1929, to the addition of potassium iodide to all salt sold in Canada. The addition resulted in a marked decrease in the iodine deficiency disorders (I.D.D.) known as cretinism and endemic goiter.

Iodides and protein-bound iodines have been used to treat various other human diseases, including hypercholesteremia, hyperlipemia, diabetes and tuberculosis. U.S. Pat. Nos. 4,187,294, 4,338,304 and 4,394,376, all to Kamimae et al. disclose a composite containing a high amount of protein-bound iodine for the treatment of hypercholesteremia, diabetes and hyperlipemia, respectively. U.S. Pat. No. 4,259,322 to Lim discloses tuberculosis medication containing sodium iodide administered by intramuscular or intravenous injections.

Recent investigations have indicated that the iodine molecule is involved in the function of various organs in the body, including the salivary glands, the stomach, the liver, the ovaries, endometrial tissues and the human female breast. Iodine deficiency appears to cause an increase in carcinogenesis when a known breast carcinogen is given to susceptible rats. In some studies, earlier onset of cancer is seen, and in others, a greater number of breast tumor sites and an increased size of tumor have been described.

Yunbing et al. related hyperplastic cystic disease of the breast etiologically to dysfunction of the ovaries with elevated estrogen level coupled with decreased progesterone level and abnormal reactivity of breast tissue to estrogen. Treatment of mammary dysplasia was directed to restoring normal ovarian function and hormonal balance of the gonad using traditional Chinese medicines. These medicines include Sargassum which contains a high iodide concentration principally in the form of potassium iodide. Among those patients treated solely with traditional medicine, Yunbing et al. reported a cure rate of 65.4 percent. This is much below the rate quoted for this invention and not substantiated by animal testing.

The first mention of the thyroid/iodine associated with the human female breast was made in 1896, by Dr. Beatson, who treated metastatic breast cancer, with some success, using desiccated thyroid in large doses. Desiccated thyroid contains an abundance of protein-bound iodine in addition to the active hormone thyroxine.

Carcinoma of the breast is less prevalent in patients with hyperthyroidism than patients with hypothyroidism, and the survival rate in the former group is enhanced as compared to hypo or euthyroid patients.

The first association of an iodine deficiency state and benign breast dysplasia was reported by Vishnyakova and Murivieva in 1966 from Russia. They reported a 71% improvement rate in women with dysplastic mastodynia treated with potassium iodide (inorganic iodine).

Studies on rats have included iodine replacement therapy in animals made iodine deficient by a Remington iodine-free diet. Employing iodide inorganic salts (sodium iodide) in food at both normal and excessive levels as replacement, the breast dysplasia appeared to abate with a partial subsidence of epithelial hyperplasia and a loss of cystic spaces but with a continuation of the fibrosis of the syndrome.

Laboratory support for the relationship of benign fibrocystic disease and iodine deficiency was furnished by Eskin reported in 1970 in the *Annals New York Academy of Science Journal*, which is incorporated herein by reference. Eskin was attempting to produce carcinoma in rat models with iodine deficiency, hypothyroidism, estrogen addition and a carcinogen. These laboratory studies were successful, but in the cellular steps to final neoplasia, microscopic changes resembling those of fibrocystic disease were produced. These changes included epithelial hyperplasia associated with mammary ducts and acinar cells, cyst formation and an increase in interacinar fibrosis. All previous animal models produced with hormonal manipulation produced hyperplasia with some cystic dilation but without the interacinar fibrosis that is characteristic of the human condition.

Other iodine-deficient disease states for which effective treatments have not been discovered include endometriosis and premenstrual syndrome.

Endometriosis is characterized by hormonally responsive endometrial tissue implants in extra-uterine sites. The etiology of endometriosis is thought to be the transplantation of uterine lining cells through the fallopian tubes, the lymph channels and/or the blood stream to the abdominal cavity. Another suggested theory is that the peritoneum undergoes metaplasia to produce endometrial cells without direct access to cellular transplants. The transplanted or transformed islands of endometrial tissue act in a similar fashion to the uterine cells, with swelling and then bleeding at the time of menstruation.

Current treatment modalities for endometriosis are directed at the normal fluctuations of the estrogen/ progesterone complex. Medications include birth control pills, masculinizing hormones such as danazol, or estrogen suppression drugs such as tamoxifen. In severe cases, total abdominal hysterectomy is the only therapy that is effective. All of the medical therapies are anti-estrogen.

Premenstrual syndrome is defined as the cyclic recurrence in the luteal phase of the menstrual cycle of a combination of distressing physical, psychological and/or behavioral changes, of sufficient severity to result in deterioration of interpersonal relationship and/or interference with normal activities. The symptoms of premenstrual syndrome include breast pain, swelling and tenderness, lower abdominal bloating, constipation, increased appetite with cravings for salt or chocolate, fatigue, emotional lability with temper tantrums, anger or crying, depression, anxiety with tension, irritability with tendency to seek confrontations, aversion to sexual relations, insomnia, confusion and/or violence.

Although premenstrual syndrome has been classified as a psychiatric instability in the premenstrual phase, psychiatric counselling has not proven to be an effective treatment. Other treatment modalities include progesterone administration, tranquilizers and pain control medication, surgical removal of the ovaries and naloxone administration. However, these other treatment modalities are also usually ineffective.

Other diseases or disorders, which are associated with increased ovarian function and/or estrogen production include breast cancer and ovarian cysts.

The nomenclature of iodine-containing compositions is ambiguous, and often misleading. Iodine is most often administered in an inorganic iodide form or as protein-bound iodine. Both of these forms utilize the $I^-$ ion and are not elemental iodine ($I_2$).

However, in the literature, both of these forms have been referred to as iodine, which to the unskilled reader might connote the use of elemental iodine ($I_2$). Prior to its use by the current inventors, elemental iodine ($I_2$) in a pure solution has not been administered as a medication specifically to treat iodine deficiency states.

Elemental iodine in a suspension form (i.e. containing micro and macro particles of iodine) has been used to treat thyroid conditions as taught by Polley in U.S. Pat. No. 4,384,960. However, such a suspension is an undesirable form of iodine. The iodine particles cause the suspension to be of unknown strength. Furthermore, the iodine particles cause the unwanted side effects of nausea, vomiting and diarrhea when the suspension is administered to patients. The iodine particles are present in the Polley suspension due to the method of manufacture which comprises direct exposure of iodine pellets, crystals or dust to water through a porous container.

SUMMARY OF THE INVENTION

This invention relates to a composition comprising elemental iodine for use in the treatment or prevention of an iodine-deficiency disease or disorder in a mammalian patient. According to the present invention, the iodine deficiency disease or disorder is selected from the group consisting of fibrocystic dysplasia, breast cancer, endometriosis, premenstrual syndrome and ovarian cysts.

According to a further embodiment of the present invention, there is provided a method for therapeutically treating or preventing an iodine deficiency disease or disorder in a mammal in need thereof. Further, according to this embodiment of the present invention, there is provided a method for therapeutically treating or preventing an iodine deficiency disease or disorder selected from the group consisting of fibrocystic dysplasia, breast cancer, endometriosis, ovarian cysts and premenstrual syndrome, comprising administering to a mammal in need thereof a sufficient amount of elemental iodine.

In a further embodiment of this invention, there is provided a method for therapeutically treating or preventing an iodine deficiency disease or disorder selected from the group consisting of fibrocystic dysplasia, breast cancer, endometriosis, ovarian cysts and premenstrual syndrome comprising administering to a mammal in need thereof from about 0.01 to about 0.20 milligrams of elemental iodine per kilogram of body weight.

In a further embodiment of this invention, there is provided a method for therapeutically treating or preventing an iodine deficiency disease or disorder selected from the group consisting of fibrocystic dysplasia, breast cancer, endometriosis, ovarian cysts and premenstrual syndrome, comprising administering to a mammal in need thereof from about 0.03 to about 0.16 milligrams of elemental iodine per kilogram body weight.

In a further embodiment of this invention, there is provided a method for therapeutically treating or preventing an iodine deficiency disease or disorder selected from the group consisting of fibrocystic dysplasia, breast cancer, endometriosis, ovarian cysts and premenstrual syndrome, comprising administering to a mammal in need thereof from about 1 to about 20 of milligrams of elemental iodine per day.

In a further embodiment of this invention, there is provided a method for therapeutically treating or preventing an iodine deficiency disease or disorder selected from the group consisting of fibrocystic dysplasia, breast cancer, endometriosis, ovarian cysts and premenstrual syndrome, comprising administering to a mammal in need thereof from about 2 to about 12 milligrams of elemental iodine per day.

BRIEF DESCRIPTION OF THE DRAWINGS

FIG. 1 shows the breast tissue from a human female with fibrocystic disease showing epithelial hyperplasia, cystic spaces and increased fibrous tissue;

FIG. 2 shows breast tissue from a normal female rat showing normal cellular configuration;

FIG. 3 shows breast tissue from a female rat rendered iodine deficient showing cystic spaces, epithelial hyperplasia associated with duct and acinar cells and increased fibrous tissues;

FIG. 4 shows breast tissue from a female rat on an iodine deficient diet with estrogens added to the model;

FIG. 5 shows breast tissue from a female rat on a normal iodine containing diet with estrogens added;

FIG. 6 shows breast tissue from a female rat on an iodine deficient diet with a carcinogen (dimethyl benzanthracene) added to the model therapy thereby producing carcinoma;

FIG. 7 shows breast tissue from a female rat on an iodine deficient diet and then given sodium iodide as a replacement treatment;

FIG. 8 shows breast tissue from a female rat on an iodine deficient diet and then given Caseo Iodine (Iodaminol, Trade Mark of Desbergers Ltee, Montreal), as replacement treatment;

FIG. 9 shows breast tissue from a female rat on an iodine deficient diet and then given elemental iodine as replacement treatment;

FIG. 12 illustrates the characteristics of a study group treated with elemental iodine;

FIG. 13 illustrates a comparison of results of replacement therapy with caseoiodine versus elemental iodine (Denovo Group);

DETAILED DESCRIPTION OF THE INVENTION

A. Iodine Treatment of Fibrocystic Dysplasia

Figure 1:
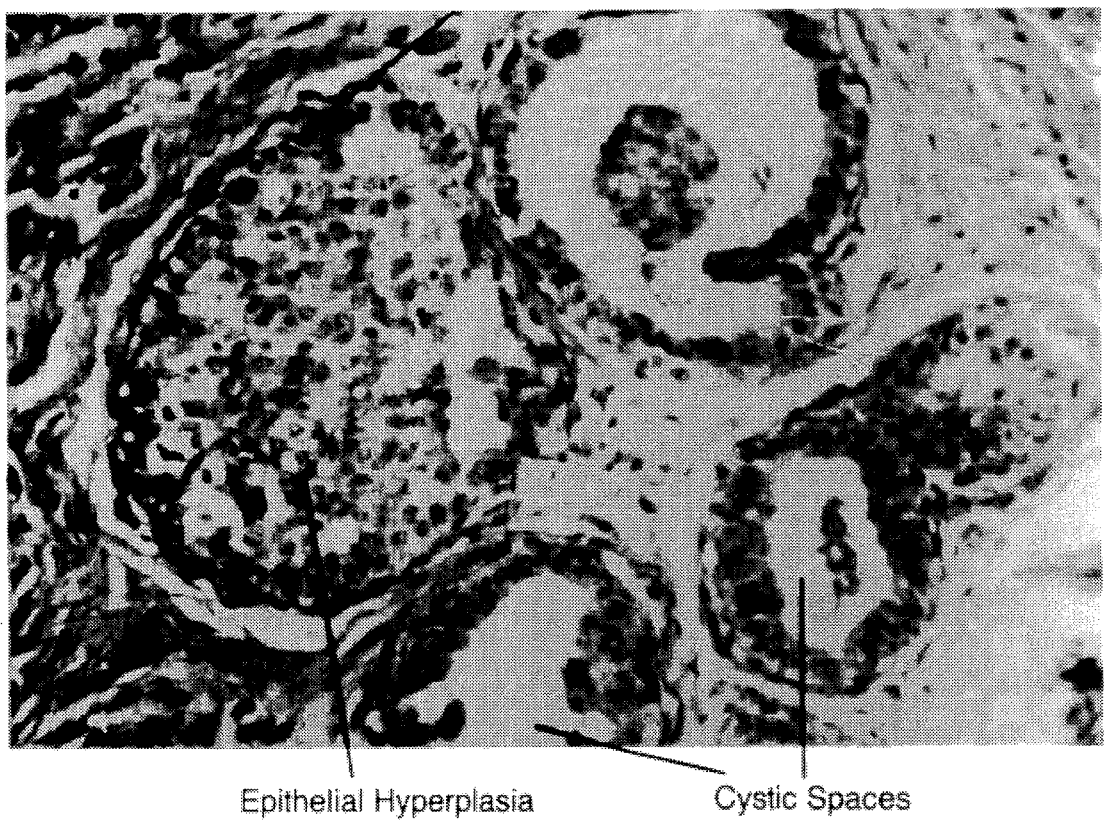
FIGS. 1 to 9 show phase-contrast photomicrographs of human or rat female breast tissue showing normal cell configuration or abnormal cell development characteristic of fibrocystic disease.

The present invention provides a method and composition for use in the treatment or prevention or iodine deficiency diseases or disorders comprising elemental iodine ($I_2$). The iodine deficiency diseases are selected from fibrocystic dysplasia, breast cancer, endometriosis, ovarian cysts or premenstrual syndrome.

In the treatment of fibrocystic dysplasia, the use of elemental iodine results in not only the relief of pain associated with the disease, the regression of epithelia hyperplasia, and the dissipation of cysts, but additionally the control and dissolution of the fibrous tissue.

The present invention further provides a method and composition for the treatment or prophylaxis of breast cancer. Particularly, element iodine ($I_2$) interacts with breast estrogen receptors to reduce the prevalence of breast cancer in susceptible mammals and halts neoplastic changes in mammals with malignant breast cancer.

The present invention further provides a method and composition for the treatment of endometriosis. Particularly, elemental iodine ($I_2$) neutralizes the ovarian function and estrogen production to control endometriosis and alleviate its symptoms.

In a further aspect of the present invention, a method and composition for the treatment of premenstrual syndrome is provided. Particularly, elemental iodine neutralizes the ovarian function and estrogen production to alleviate the symptoms of premenstrual syndrome.

The present invention is also directed to the treatment or prevention of ovarian cysts. Particularly, elemental iodine neutralizes the ovarian function and estrogen production to reduce or eliminate the occurrence of ovarian cysts.

For the purpose of this application, elemental iodine refers to diatomic iodine ($I_2$) which may also be referred to as metallic iodine or iodine metal. In an effort to overcome the disadvantages of the prior art, the present invention provides a pharmaceutically acceptable form of elemental iodine, which may be administered orally, without the vile taste of previous replacement compositions, notably Lugol's iodine (potassium iodide in aqueous solution), and without the side effects associated with various prior art treatments. According to the present invention, elemental iodine can be admixed with a suitable pharmaceutical carrier for oral administration. The pharmaceutical carrier can be a solid carrier such as lactose, starch, sugar, gelatin, cellulose or other nonmedical ingredients, either alone or in mixtures thereof.

Thus, according to the present invention, elemental iodine is meant to include any pharmaceutically acceptable form of elemental iodine which can be administered orally.

Elemental iodine can also be prepared as an aqueous solution of $I_2$ in water or other physiological aqueous vehicles. According to the present invention, elemental iodine in an aqueous solution is produced by a unique method which prevents any micro or macro particles of iodine from being present in the solution. Iodine crystals are placed in a sealed plastic bag or container which is exposed to water at about 20° C. The iodine crystals sublime, and iodine vapor passes through the plastic and into the water to produce a pure solution of elemental iodine without any particulate matter.

The particular plastic composition used must be penetrable by iodine vapor but impermeable to water and micro or macro particles of iodine. The inventors have found that suitable plastics include polyethylene, polypropylene, polybutylene and related plastic compositions. A preferred plastic composition is a 1 millimeter thick film of linear, low density polyethylene.

The concentration of the pure solution after the iodine vapor has passed through the plastic to the water is about 270 milligrams elemental iodine per liter of solution to about 350 milligrams of elemental iodine per liter of solution. A preferred concentration is 300 mg of elemental iodine per liter of solution.

As stated above, the pure solution with the required concentration is obtained by exposing a plastic container of prilled iodine to water for an amount of time sufficient to yield a pure iodine solution with a concentration of about 270 to about 350 milligrams elemental iodine per liter of solution. The temperature of the water effects the rate of sublimation of the prilled iodine, and therefore effects the time to stabilization of the pure solution at the required concentration. Preferably, 7 grams of prilled iodine is placed in a polyethylene container, and submerged in 100 ml of distilled water at about 20° C. for about 18 hours to produce a pure iodine solution having the required concentration (about 270 to about 350 milligrams elemental iodine per liter of solution).

Alternatively, the polyethylene container with 7 grams of prilled iodine is submerged in 100 ml of distilled water at about 50° C. for about 30 minutes to obtain the pure solution having the required concentration. At 50° C., the prilled iodine sublimes at a much faster rate.

Once the pure solution has been produced, it is an easy process for the patient to replenish the solution after use. Refilling a partially used dispenser of the solution with distilled water at 20° C. results in further sublimation of the prilled iodine in the polyethylene container, and stabilization of the solution at the required concentration occurs in about 6 hours.

The pure elemental iodine solution produced by the above-described methods allows an accurate dosage regime to be maintained, and reduces the unwanted side effects of nausea, vomiting and diarrhea. Both of these advantages are attributable to the lack of particulate iodine in the solution.

Breast dysplasia and neoplasia are influenced by the available iodine ion. Carcinogenesis occurs early in estrogen therapies in association with iodine deficiency.

The subsequent addition of iodine to iodine-deficient diets in rat experiments reversed breast dysplasia. Once breast lesions were established, only chronic iodine replacement manages the dysplasia that is formed.

The first iodine product used in the reversal experiment was sodium iodide. The use of sodium iodide resulted in reversal of the pathological changes to a degree with the partial subsidence of cyst formation, epithelial hyperplasia and fibrosis. The interacinar fibrosis remained.

Iodine caseinate, an organified form of iodine was next tested based on the proven ability of the breast tissue to deorganify iodine to secrete iodine as in organic potassium iodide in milk. The breasts' ability to organify inorganic iodine with the addition of protein molecules, some in the form of thyroxin, was proven by Eskin and reported in "Iodine in Breast Cancer-A 1982 Update" in *Biological Trace Element Research* 538.

The testing of iodine caseinate on the rat model, which first began in 1974, resulted in a reversal of the cyst formation and the epithelial hyperplasia. The interacinar fibrosis remained as a hallmark of continuing pathology.

Iodine replacement therapy investigations have been limited to animal experimentation until recently. Since the basic research had shown changes resembling fibrocystic disease in women when iodine was deficient, the clinical analogy became apparent. The clinical application of this basic research was started in 1969. Clinical treatment of women with fibrocystic disease was carried out using Lugol's solution (Strong Iodine Solution, U.S. Pat.), which is a solution containing 5% by weight iodine and 90% by weight potassium iodide. Undesirable characteristics of Lugol'iodine are that it has a vile taste and has the potential to disrupt thyroid function because of the presence of large quantities of sodium iodide. With the discovery of iodine caseinate as a viable replacement for Lugol's ,solution, it became the basic treatment modality beginning in 1974.

This protein-bound iodine, Caseoiodine-Iodaminol was administered in doses of 10 mg per day and resulted in an improvement rate of over 90%. These therapeutic trials by Ghent were enlarged in 1985 to 588 Caseoiodine patients. The patients treated with iodine caseinate experienced definite improvement both subjectively and objectively. Forty-three percent were symptom free and their breasts had returned to normal. Fifty percent had residual premenstrual discomfort and fibrous tissue collections on examination. (Caseoiodine has a small amount of free $I_2$ in its composition). In addition to the very favorable results obtained through the treatment of fibrocystic disease by iodine replacement therapy, Ghent's patients did not have the massive side effects reported by Greenblatt in his treatment of mammary dysplasia with danazol, as reported in *Fertil, Steril* 34, 1980.

Most recently (in August of 1984), clinical testing was begun by Ghent for the treatment of fibrocystic dysplasia using an oral administration of elemental iodine. As a result of treatment with aqueous iodine, 90% of patients treated have experienced dramatic reduction in breast size caused by cystic formation and reduction of the fibrosis and pain associated with this syndrome.

These clinical results parallel the laboratory results obtained in tests run concurrently by Eskin in Philadelphia. Thin section photomicrographs of breast tissue from female rats show not only the control of cysts, including the abatement of epithelial hyperplasia but additionally, the control and dissolution of the fibrous tissue characteristic of fibrocystic disease. Heretofore, the complete reverse of fibrocystic disease was not experienced using iodine replacement therapy. Only treatment with aqueous iodine resulted in the complete reversal of the fibrocystic dysplasia, including the control of fibrosis and thus a return to normal.

FIG. 1 is a photomicrograph of the breast tissue of a human female. This photomicrograph illustrates epithelial hyperplasia, cyst formation and increased fibrous tissue associated with fibrocystic disease. Laboratory studies on rats by Eskin allow for a comparative study of the relative effect of the various prior art iodine replacement therapy, including sodium iodide, iodine caseinate, and elemental iodine as a treatment for fibrocystic disease, as illustrated by the other figures.

Figure 2:

FIG. 2 is a photomicrograph of a normal female rat illustrating normal cellular configuration. The breast tissue includes a predominance of adipose tissue with no exhibition of epithelial hyperplasia, cyst spaces or fibrous tissue.

Figure 3:
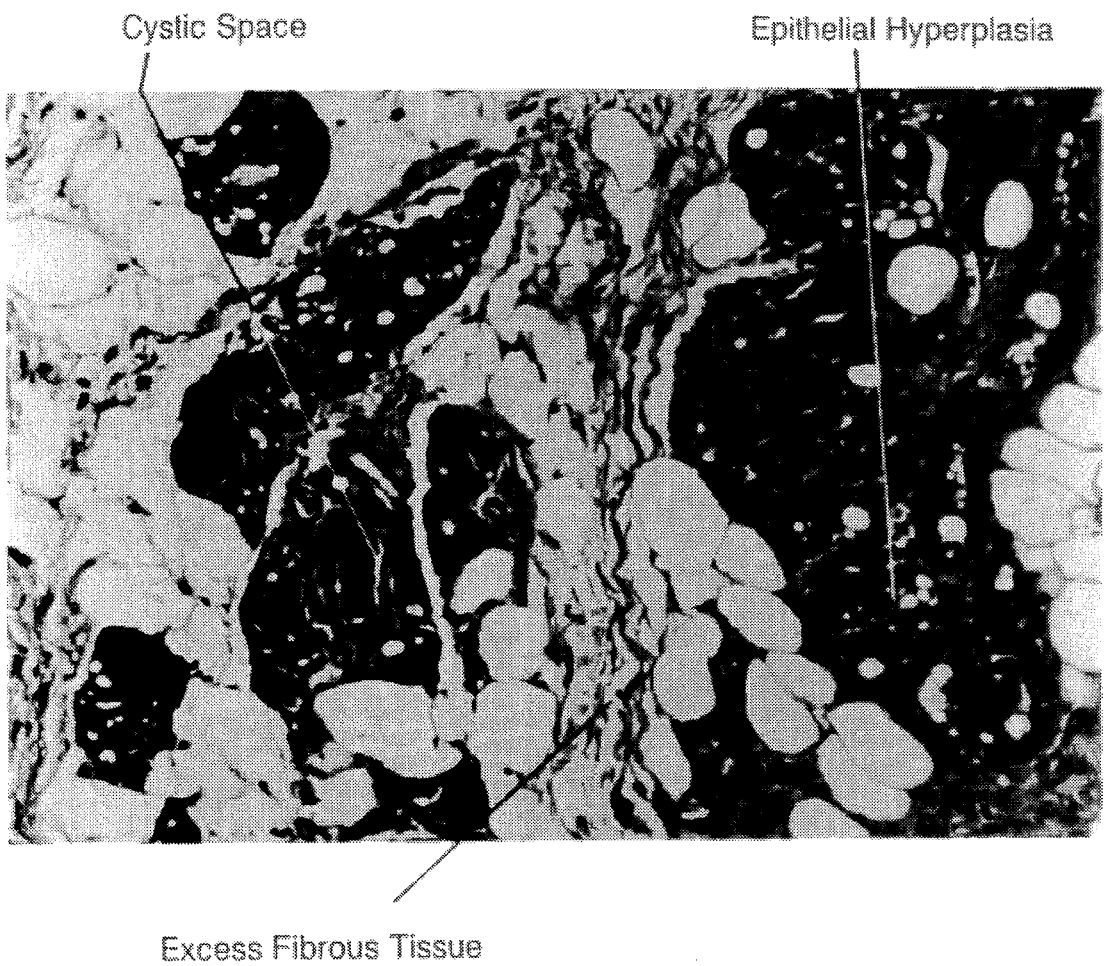

In comparison, FIG. 3 illustrates rat breast tissue rendered iodine deficient. The iodine deficient breast tissue shows cystic spaces, epithelial hyperplasia and increased fibrous tissue characteristic of fibrocystic dysplasia. The comparison of FIGS. 2 and 3 support Eskin's previous findings relating iodine deficiency to fibrocystic disease first reported in 1970 in the *Annals New York Academy of Sciences Journal*, Series II, Volume 32, 1970; 911–947 and updated in *Iodine and Breast Cancer—A 1982 Update, Biological Trace Element Research*, Volume 5, 1983, 399–412. The material disclosed in these articles is incorporated herein by reference.

Figure 4:
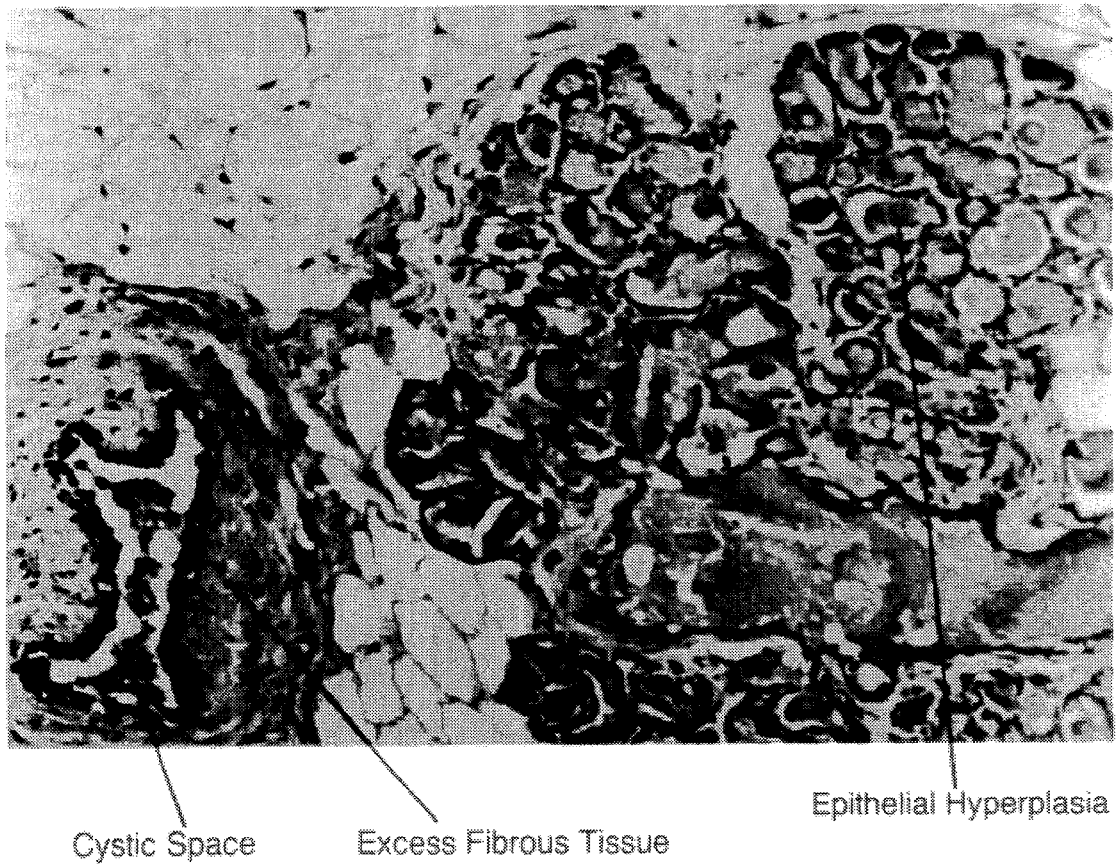
Figure 5:
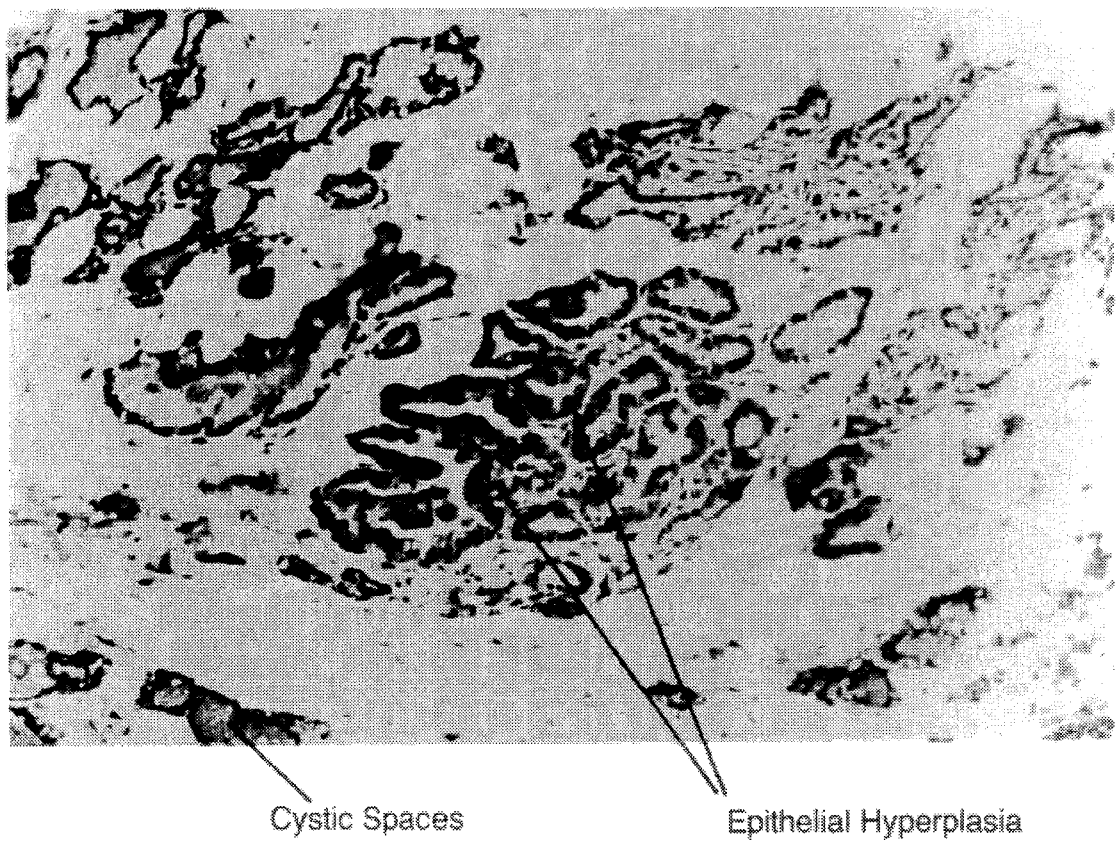

FIGS. 4 and 5 show the effect of estrogens on the breast tissue from a female rat which was on an iodine deficient diet. FIG. 4 illustrates an enhancement of cystic spaces, marked increase in epithelial hyperplasia and increased fibrosis between the secreting acini. This inconsistent with the findings of Fratkin reported in the paper entitled "The Hyperoestrogen State" presented at North Pacific Surgery Meeting in Tacoma, Wash. in 1980. A correlation was established between fibrocystic dysplasia and increased estrogen intake in milk drinkers. FIG. 5 is illustrative of the effect of estrogens when added to the breast tissue from a female rat which was on a normal iodine containing diet. The control rat shows some cyst formation and epithelial hyperplasia but without the fibrosis present in the tissue of the rat on the iodine deficient diet.

Figure 6:
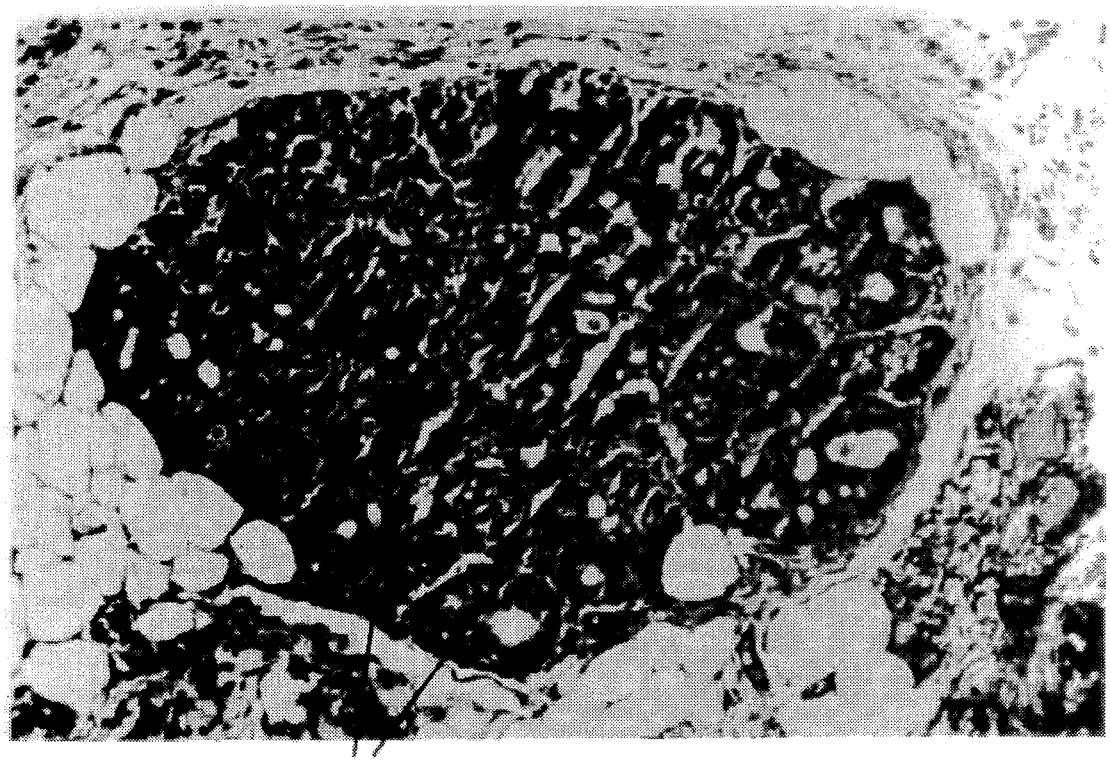

The addition of the carcinogen, in this case dimethyl benzanthracene, to the breast tissue from a female rat on an iodine deficient diet, results in the progression from the benign state of fibrocystic dysplasia to overt malignancy as seen in FIG. 6. This finding is supportive of the inventors' contention that fibrocystic disease enhances the risk of breast cancer causing sensitization of the breast tissue to various stimuli, including carcinogens. This sensitization process may explain the increased incidence of breast cancer in women in areas of deficient iodine intake, reported by Moosa et al. in "Thyroid Status and Breast Cancer", Royal College of Surgeons, England, 53, 1975.

Figure 7:
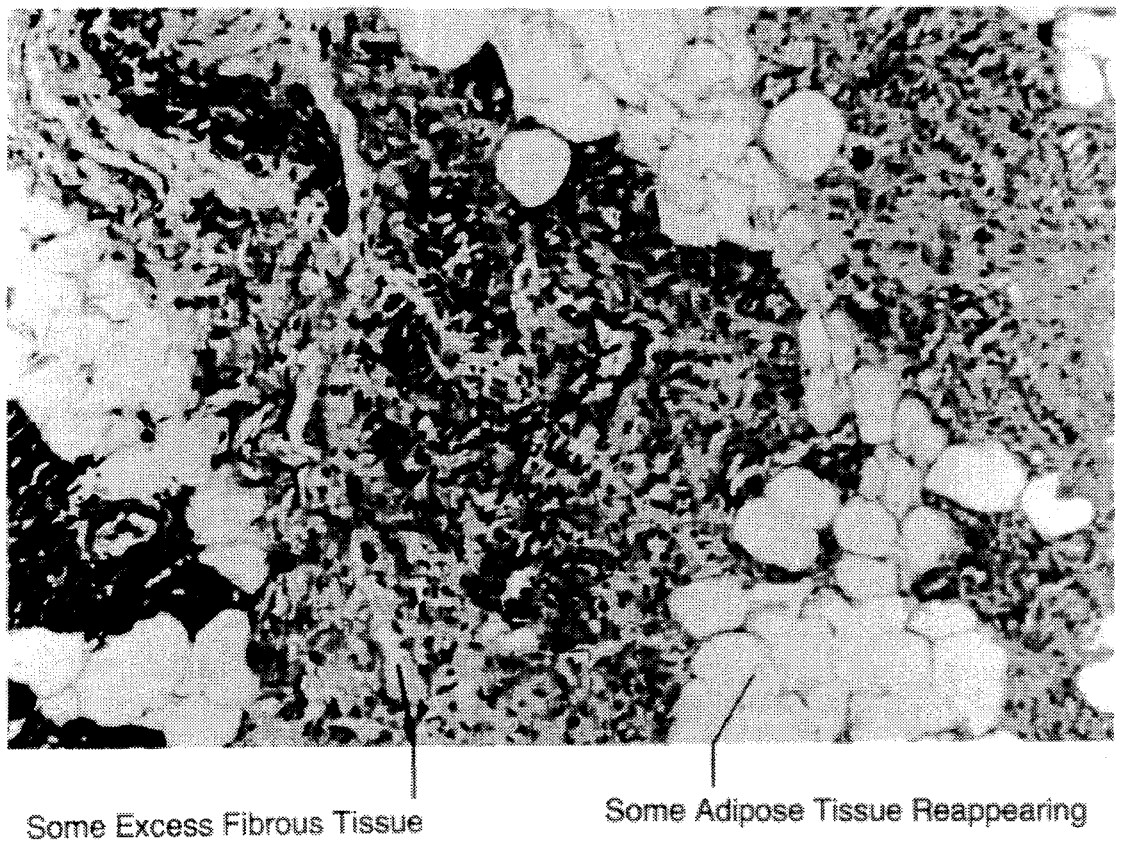

FIG. 7 illustrates the effect of sodium iodine as a replacement treatment on breast tissue from a female rat which was on an iodine deficient diet. The epithelial hyperplasia regressed and the cystic spaces disappeared, but the fibrous tissue remained. This is consistent with the inventors' initial research on iodine replacement therapy for fibrocystic dysplasia beginning in 1969.

Figure 8:
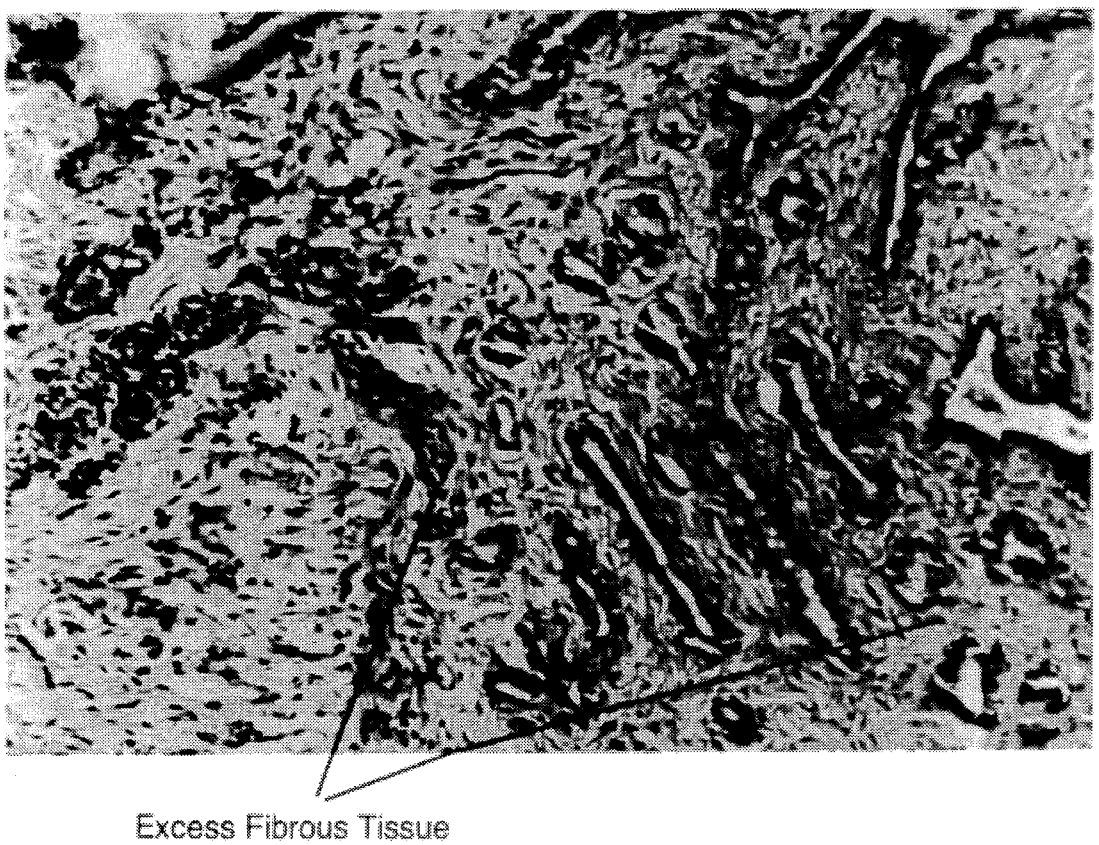

The effect of iodine caseinate on the morphology of rat breast tissue is illustrated in FIG. 8. This figure shows the subsidence of the epithelial hyperplasia and the reduction in cystic spaces, however the fibrosis remains unchanged.

Figure 9:
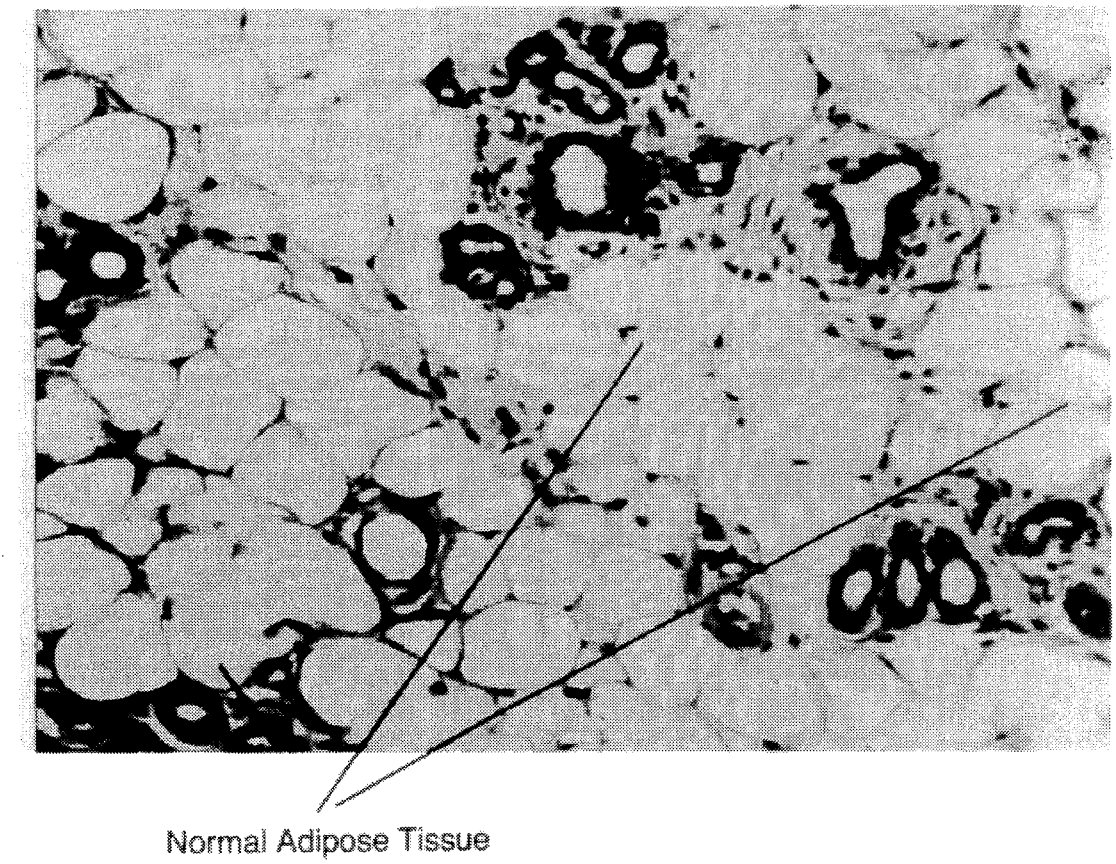

In comparison, replacement treatment with elemental iodine is shown in FIG. 9. This figure shows a reversal of tissue morphology to near normal with the return of normal adipose tissue components, subsidence of the epithelial hyperplasia and cyst spaces, and most notably, subsidence of the fibrosis (see also FIG. 2 for comparison). Heretofore, other forms of iodine replacement treatment of fibrocystic dysplasia have not been successful in the control and reversal of fibrosis. This was clearly an unexpected result.

Parallel clinical testing by Ghent supports the laboratory findings of Eskin. Iodine replacement therapy with elemental iodine began in August of 1984. At that time, 142 women with fibrocystic disease were treated with aqueous iodine. Eighty of these women were patients who had been on iodine caseinate therapy for varying periods of time and had a resolution of the cystic component but with the continued existence of fibrosis. The remainder of the sample group were patients who were started on aqueous iodine replacement therapy as the first form of treatment.

Clinical observations of the 142 cases of fibrocystic dysplasia indicated that both groups of patients had uniformly good results. The first group still had some residual discomfort and some lumpiness from the fibrosis during their treatment with iodine caseinate. However, the pain was relieved in 90% of the patients in 4 to 16 months after being switched to aqueous iodine treatment. In addition, the patients indicated that their breasts were softer and had reduced in size by ¼ to 2 cups in brassiere size. This is indicative of the reversal of the fibrosis.

The second group consisting of de novo patients, had similar dramatic results in 4 to 16 months with control of pain, control of cysts, and control of fibrosis. These patients also noted a decrease in breast size by ¼ to 1½ cups (brassiere size). This result was obtained in 90% of the patients treated.

The initial results of elemental iodine therapy were encouraging with a resolution of all the elements of the triad (see FIG. 9). These results initiated further clinical testing on human volunteers suffering from fibrocystic disease. Of these, two hundred fifty-three to date have had sufficient follow-up to allow analysis.

It has been found that a daily dose of about 1.0 milligrams to about 20 milligrams of elemental iodine ($I_2$), with a suitable pharmaceutical carrier, is effective in the treatment or prevention of iodine deficiency diseases. A daily dosage of 2 to 12 milligrams of the elemental iodine has also been found to be effective in the treatment or prevention of iodine deficiency diseases. A daily dosage of about 3 milligrams to about 6 milligrams of the elemental iodine has further been found to be effective for the treatment or prevention of iodine deficiency diseases. The exact dosage can be selected depending upon the patient's needs, as determined by the practicing physician.

Based on the body weight of the patient, it has been found that a daily dosage of 0.01 to 0.20 milligrams of elemental iodine, in a suitable pharmaceutical carrier, per kilogram body weight of the patient is effective for the treatment or prevention of iodine deficiency diseases. It has further been found that a daily dosage of from about 0.03 milligrams to about 0.16 milligrams of the elemental iodine per kilogram of body weight of the patient is effective for the treatment or prevention of iodine deficiency diseases. It has further been found that a daily dosage rate of about 0.07 milligrams to about 0.09 milligrams of the elemental iodine per kilogram body weight of the patient is also effective for the treatment or prevention of iodine deficiency diseases.

In one example of the present invention, the elemental iodine can be administered as an aqueous solution. The aqueous solution preferably contains about 0.3 milligrams of elemental iodine per milliliter of solution.

In another example of the present invention, the elemental iodine can be administered as a starch iodine complex, in tablet form, wherein each tablet contains 3 milligrams of elemental iodine.

EXAMPLE 1

Elemental Iodine Therapy Study

The subjects of this study were volunteers who had been referred with nodular, painful, swollen breasts. The diagnosis of fibrocystic disease was made on clinical examination, thermography and mammography when the age of the patient permitted such diagnosis.

As shown in FIG. 12, the study group was divided into two sections. The first group, the de novo group, numbered 108 and had not been treated previously for fibrocystic disease. The second group, the transfer group, numbered 145 and had been on iodine replacement therapy with caseoiodine for a mean of thirty months but had experienced residual discomfort and fibrosis. The treatment of the transfer group was suspended and all patients in the series received 3–6 mg of elemental iodine daily.

In establishing the dosage of aqueous iodine required to effectively control all symptoms associated with fibrocystic disease, Dr. Ghent established a dosage range of about 1.2 milligrams to about 6 milligrams per day of elemental iodine in aqueous solution with 3–6 milligrams per day being the most effective dose as noted above. These dosages were based on a dosing rate of about 0.07 milligram to about 0.09 milligram of elemental iodine ($I_2$) per kilogram of the patient's body weight.

Figure 10:
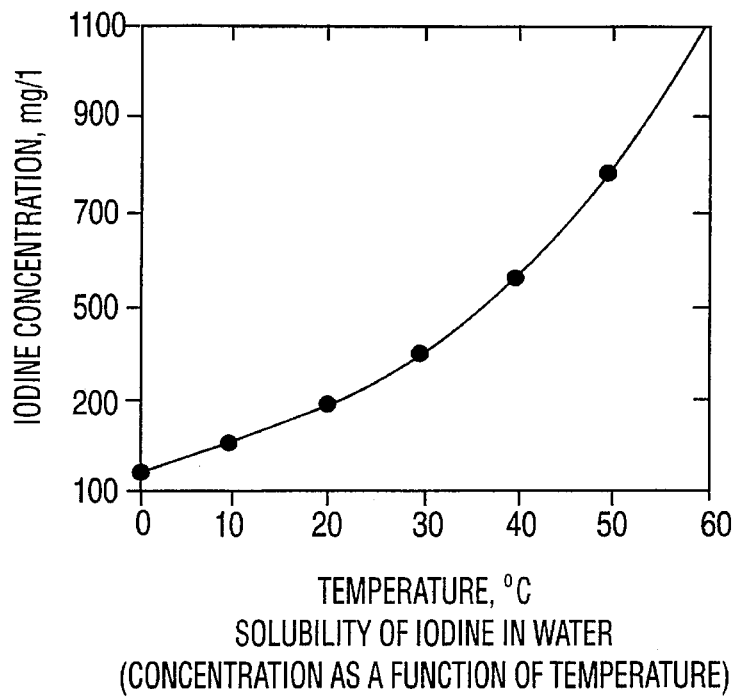
FIG. 10 illustrates the solubility of iodine in water relating the concentration of iodine as a function of temperature.

FIG. 10 shows the solubility of iodine in water and illustrates the relationship of iodine concentration as a function of temperature. This solubility curve was used to calculate the dosage range by Ghent and is taken from Black et al., "Use of Iodine For Disinfection" from *Journal of American Waterworks Association*, Volume 37, No. 11, November 1965.

Further, the half life of $I_2$ in the human appears to be eight hours and therefore a daily dose is necessary. This is supported by clinical evidence wherein 10 cases were reduced to a twice-weekly dose and within two weeks had a recurrence of symptoms. These clinical findings are supported by the inventors' previous clinical testing wherein 89.5% of patients who stopped iodine replacement therapy had a recurrence of symptoms within a nine-month period.

Figure 14:
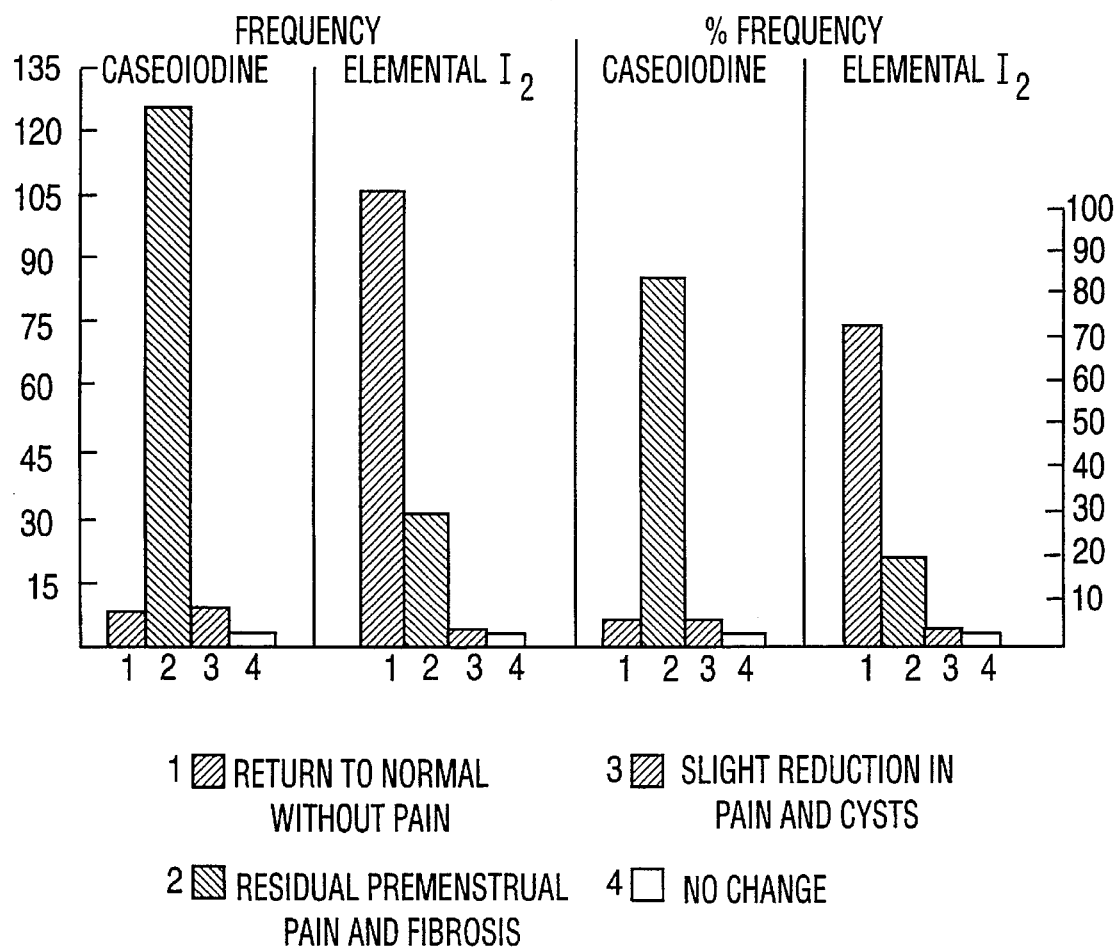
FIG. 14 illustrates a comparison of results of replacement therapy with caseoiodine versus elemental iodine (Transfer Group)

The patients of the study group were reassessed at four months and sixteen months. As shown in FIGS. 13 and 14 the results of the study were classified in four classes with Class 1 representing a subjective and objective return to normal. The patients of Class 2 had some residual discomfort and some residual fibrosis. Classes 3 and 4 were considered as poor results with continued pain, fibrosis and cysts.

The results in the de novo patients (FIG. 13) showed a complete subjective relief of breast pain and a clinical return to normal in 72% of patients with 26% retaining a small residual plaque of fibrosis at the fourth month level. As objective confirmation of the patients' changed mammary status, 76% showed a reduction in breast size that varied from ¼ to 2 cups in brassiere size.

The transfer group illustrated the most significant results with a loss of residual breast discomfort and a complete resolution of fibrosis in 74% of the cases. A smaller percentage of patients (21%) were of Class 2 experiencing minor cyclical pain and some remaining soft fibrosis (see FIG. 4). It seems that the longer the duration of the fibrocystic syndrome, the longer the time required for comfort and normalcy. Reduction in breast size was as significant as the de novo group (FIG. 13).

A further group of patients were placed on a daily treatment of elemental iodine wherein the elemental iodine was admixed with starch in the form of a starch iodine complex wherein the iodine is present as triiodide ions ($I_3^-$) or polyiodide ions ($I_5^-$ up to $I_{11}^-$). When the starch iodine complex dissociates elemental iodine ($I_2$) is released and is the effective active ingredient. This form of pharmaceutical formulation is described in detail in Applicants' copending application U.S. Ser. No. 08/272,308, filed Oct. 14, 1992 (continuation of U.S. Ser. No. 676,170, filed Mar. 28, 1991) and in published PCT Application PCT/CA92/00115 (WO92/17190) published Oct. 15, 1992.

Examples of suitable dosages for the administration of the starch iodine complex are found below in Table 1.

TABLE 1

| Patient No. | Weight (kg) | Milligrams $I_2$/Day | Milligrams $I_2$/kg bw |
| --- | --- | --- | --- |
| 1 | 81.82 | 6–9* | 0.07–0.11 |
| 2 | 71.82 | 6 | 0.084 |
| 3 | 54.55 | 6 | 0.110 |
| 4 | 95.45 | 9 | 0.094 |
| 5 | 59.09 | 6 | 0.102 |
| 6 | 57.27 | 6 | 0.105 |
| 7 | 52.27 | 3 | 0.057 |
| 8 | 56.82 | 6 | 0.106 |
| 9 | 64.55 | 9 | 0.139 |
| 10 | 68.18 | 6 | 0.088 |
| 11 | 63.64 | 6 | 0.094 |
| 12 | 68.18 | 9 | 0.132 |
| 13 | 50.91 | 6 | 0.118 |
| 14 | 55.00 | 6 | 0.109 |
| 15 | 61.36 | 6 | 0.098 |
| | | Average = | 0.103 |

*Patient was started on 2 caps/day in Sept. 92 and switched to 3 caps/day in Aug. 93.

EXAMPLE 2

Comparative Study of Caseoiodine Treatment

Figure 11:
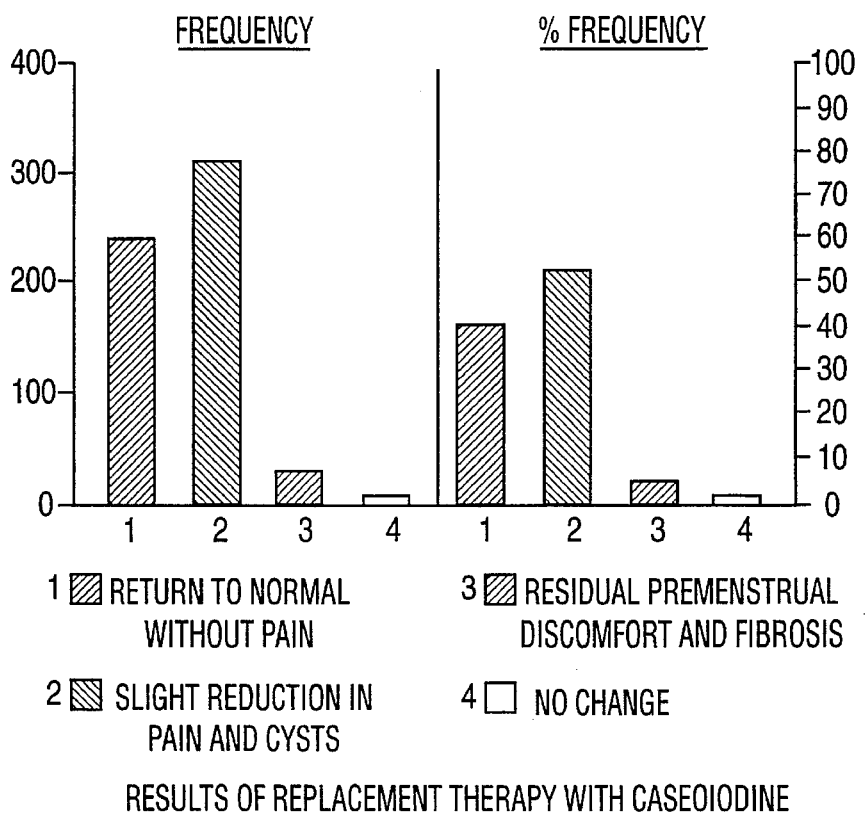
FIG. 11 illustrates the results of replacement therapy with caseoiodine.

As noted above, Ghent and Eskin in 1985 enlarged their series of caseoiodine patents to 588 with an improvement rate of 93.4%. As shown in FIG. 11, this improvement rate was categorized originally in four classes, 1–4. The first group accounted for 43% of a subjective and objective return to normal. The second group (50.4%) had some residual premenstrual discomfort and had fibrosis that at best was only worrisome but at worst could mask early malignant changes both clinically and mammographically.

A comparison of the results obtained with caseoiodine therapy and with elemental iodine therapy is revealing as shown in FIG. 14. The caseoiodine therapy resulted in the return to normal without pain in 5.4% of patients (class 1), while 85.8% of patients experienced some residual premenstrual pain and fibrosis (class 2). The results after the patients were transferred to elemental iodine therapy were significant with 73.7% of patients returning to complete normalcy (class 1) and 21.3% again experiencing residual premenstrual pain and some fibrosis (class 2) at four months evaluation. This increased to over 90% at the 16-month evaluation.

Figure 15:
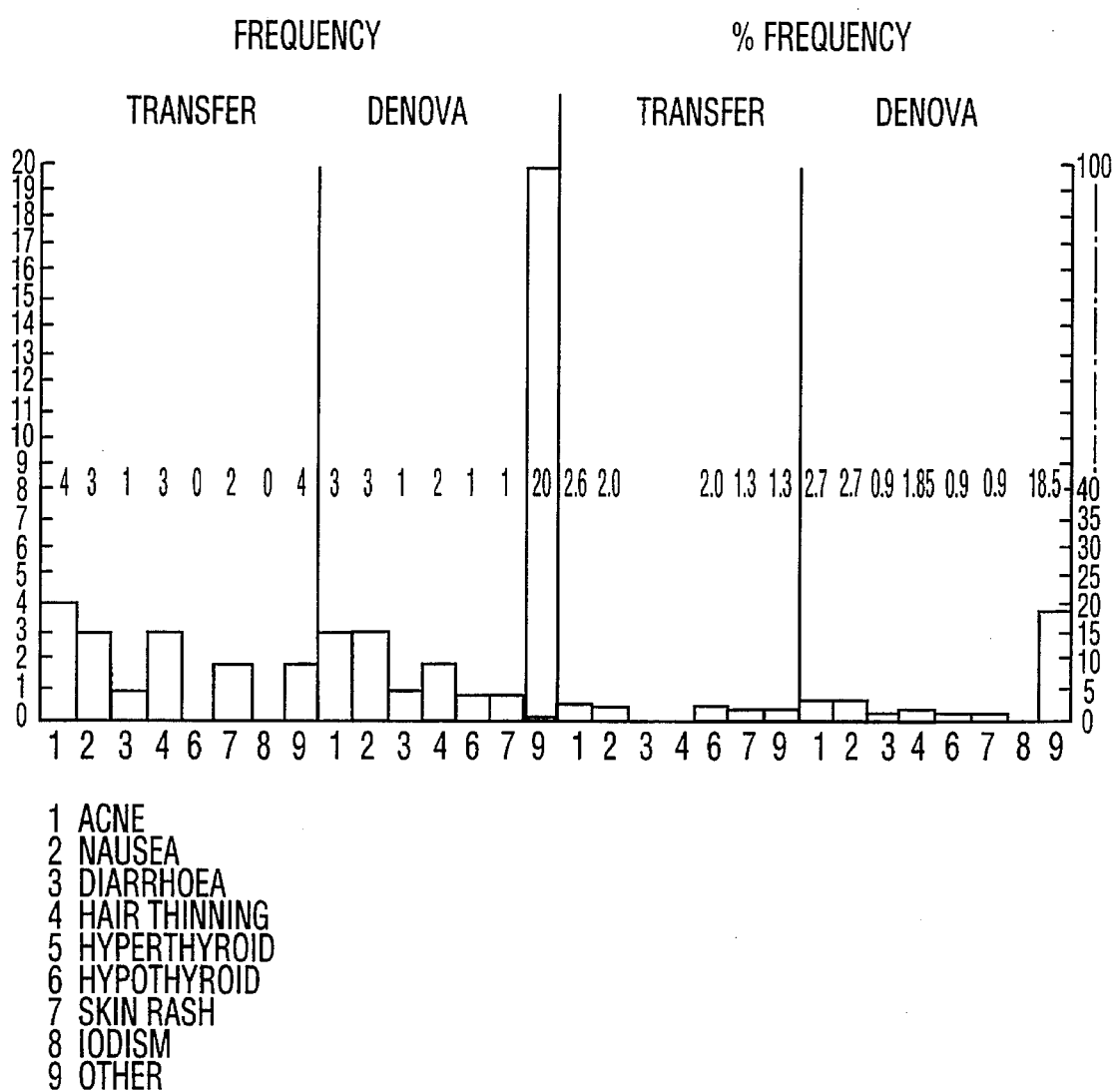
FIG. 15 illustrates the various complications manifest in the Denovo and Transfer Groups subjected to elemental iodine therapy.

The various complications of iodine replacement therapy are listed in FIG. 15. These include acne, nausea, diarrhea, hair thinning, hyper- and hypothyroidism, skin rash and iodism. An increase of pain was also experienced by patients: 18.5% of the de novo group and 1.3% of the transfer group during the treatment cycle. This pain occurred three to six weeks into the treatment regime and lasted from one to three weeks. The manifestation of pain seemed to coincide with a decrease in breast size and a sudden softening of the fibrosis. Once this pain had subsided it did not recur.

Based on the two series of clinical patients and in consideration of the various complications above, elemental iodine replacement therapy has been found to be an effective treatment regime, more effective than other forms of iodine replacement therapy, including treatment using caseoiodine. Iodine replacement therapy generally should be considered before mastectomy, hormonal manipulation or neglect.

B. Iodine As Treatment and Prophylaxis for Breast Cancer

The present invention further provides a method and composition for the treatment and prophylaxis of breast cancer. Particularly, elemental iodine interacts with breast estrogen receptors to reduce the prevalence of breast cancer in susceptible animals and halt neoplastic changes in animals with malignant breast cancer. Published clinical studies which include those of the inventors, have shown evidence of iodine metabolism within the ducts and particularly in the terminal ducts (acini) of the breast (Eskin, BA, Iodine Metabolism and Breast Cancer, *Trans NY Acad Sciences*, 32: 911, 1970; Strum, JM, et al., "Resting Human Female Breast Tissue Produces Iodinate Protein", *J. Ultrastructure Res*, 84: 130, 1983). The infrastructures of breast secretory cells have been shown to both organify iodides and to produce tyrosine/iodine compounds.

One prominent facet obtained from this research with iodine is the effect of iodine deficient conditions on rat mammary glands. This deficiency can be obtained either through the use of an iodine deficient diet and/or through perchlorate treatment. Iodine deficient, but euthyroid, rats exhibit mammary gland abnormalities which pass through transitional histological steps and resemble the fibrocystic, adenomatous, and fibrotic diseases present in women. In both rats and women these conditions are benign. Thus, the rat mammary gland serves as an excellent animal model for breast diseases.

Iodine deficiency causes a functional increase in breast estrogen receptor activities, which disappears upon iodine replacement. Intracellular biochemical pathways appear to be responsible for this result. The biochemical pathway seems to be an intracellular attraction by iodine for estrogen receptors. The pathway also calls for the presence of a small, intermediate protein which has been shown to function in active breast cells in combination with the iodine/tyrosine products. Thus, cell metabolism is altered when there is "inadequate" iodine present.

Iodides can be oxidized to iodine in the thyroid without difficulty. However, in the breast the peroxidase necessary for this transition may be lacking or inactivated (DeSombre, E. R., et al., "Identifications, Subcellular Localizations and $E_2$ Regulation of Peroxidase" *Cancer Research*, 35: 172, 1975). Further basic research in this direction indicates that a unique iodine treatment for the breast has the capability of providing normal intracellular responses.

Several iodinated compounds and chemical forms of iodine, such as caseoiodine, sodium iodide (NaI) and potassium iodide (KI) have been tried for treating the resulting histopathologies from iodine deficiency over the past ten years with only minimal success. However, the inventors have found that when aqueous or diatomic iodine is used, the histopathology in the breast becomes normal.

Trials were first performed on a rat model, and then on women for this benign condition. The results show that diatomic iodine should be considered efficacious for the treatment of the fibrocystic diseases of the breast (Eskin, B. A., et al., "Etiology of Mammary Gland Pathophysiology Induced By Iodine Deficiency"*Frontiers in Thyroidology* (Eds: Madiero-Noto, G. and Gatan, E.), New York: Plenum, 1986, p. 1027; Ghent, W. R., et al., "Fibrocystic Breast Dysplasia: A Deficiency Syndrome", *Clin Invest Med* (Canada), 9: A66 (R406), 1986; Ghent, W. R., et al., "Elemental Iodine Supplementation in Clinical Breast Dysplasia", *Proc Am Asso Ca Res*, 27: 189 (751), 1986)).

The therapeutic iodine studies in women were originated after basic research in the mammary glands of rats. Iodine in its elemental form shows early evidence of effectiveness against neoplasia in the mammary glands.

The interaction between iodine and the breast is not simply conjecture. Morbidity and mortality incidences in iodine deficient regions of the world have been shown to be above average for breast diseases (benign and malignant). Regions with adequate or excessive iodine levels have much lower incidences of breast diseases. Iodine deficient regions in the United States and Canada (described by the World Health Organization) similarly show a much higher census of breast cancer.

Early studies conducted by the inventors have shown iodine deficiency appears to cause an increase in carcinogenesis when a known breast carcinogen is given to susceptible rats. In some studies, earlier onset of cancer is seen and in others a greater number of breast tumor sites and an increased size of tumor have been described. Early attempts at replacement with available iodides were partially responsive but in most cases they were actually totally ineffectual. This situation is similar to that seen when benign diseases were initially treated using a rat model.

Iodine seems to be a requirement for normal cellular growth and metabolism in the breast. Breast tissues may be iodine deficient, although adequate iodides are present for thyroid or other tissue needs. However, the unique biochemical pathway found in the breast seems to respond best to replacement with diatomic (elemental) iodine ($I_2$).

The daily dosage with elemental iodine $I_2$ for treatment or prophylaxis of breast cancer in humans is the same as that for the treatment of fibrocystic dysplasia, namely about 1.0 milligrams to about 12 milligrams of elemental iodine in a pharmaceutical carrier. In one example of the present invention, a daily dose of about 3 milligrams to about 6 milligrams of elemental iodine was provided administered as an aqueous solution containing about 0.3 milligrams of elemental iodine per milliliter of solution. These dosages are based on a dosage rate of about 0.01 milligrams to about 0.20 milligrams elemental iodine ($I_2$) per kilogram of patient body weight. The precise dosage will depend upon the patient's needs, as determined by the practicing physician. In the treatment of breast cancer, these daily doses will cause the subsidence of neoplastic changes in breast tissue, and when used for the prophylaxis of breast cancer, these daily doses will reduce the prevalence and the volume of breast cancer.

IODINE TREATMENT OF BREAST CANCER

EXAMPLE 3

Spontaneous Breast Cancers in Rats

Since several different iodide modalities were used for evaluation without success, a preliminary study using iodine (diatomic, elemental) was begun by the inventors. This study employed Sprague-Dawley rats under severely iodine deficient conditions. The latter was obtained by using both dietary and perchlorate treatment together. While most of the histopathology obtained in the control rat group was noted to have only severe breast dysplasia, approximately 9% had evidence of neoplasia with cytological aberrations consistent with malignant alterations. When diatomic iodine was administered at a dosage of 0.5 mg per 100 gm body weight (orally) to the experimental groups, the breasts were noted to have improved and there was no evidence of persisting neoplastic changes in any of the rats.

EXAMPLE 4

Iodine Treatment of Induced Breast Tumors in Rats

DMBA, a carcinogen, causes mammary gland neoplasia in rats. If these tumors contain breast peroxidase, they respond to iodine and estrogen treatment. However, as the tumors become less responsive to iodine (hormone independent), breast peroxidase is found to be lacking.

The use of perchlorate as a peroxidase-blocking agent increases the tumorigenesis and the effectiveness of iodide therapy. Preliminary studies with diatomic iodine at a dosage of about 0.5 mg per 100 gm body weight (orally or intraperitoneally) have shown the tumors to be more response to both diatomic iodine and estrogen.

In basic research studies, elemental iodine has been shown to be necessary for normal estrogen receptor function in rats. A characteristic of breast cancer is the change in response to estrogen and estrogen receptor variability.

EXAMPLE 5

Prophylaxis Against Breast Cancer with Iodine

The incidence of breast cancer in women who had been treated with elemental iodine is less than the incidence of breast cancer in women who had not been so treated. The incidence of breast cancer in women treated with elemental iodine was compared with other published results, namely the results as published by the Ontario Cancer Research, and results published by Spratt. These results are shown below:

Ontario Cancer Research—$16.50 \times 10^{-4}$ cancers per women year (From Ontario Cancer Treatment and Research Foundation, 1987, Table II, page 184)

Spratt's series—$16.40 \times 10^{-4}$ cancers per women year (Journal of Surgical Oncology, Vol. 41, page 42, 1989)

Ghent series—$6.25 \times 10^{-4}$ cancers per women year (Dr. Ghent's clinic, Kingston, Ontario)

Evidence for the diatomic iodine replacement thesis was obtained in a prophylactic treatment regime where simultaneous therapy with diatomic iodine as described in Example 3 above, was given to a limited number of prepared rats. The mammary glands showed no neoplasia secondary to this low iodine diet/perchlorate treatment. This preliminary study showed that diatomic iodine appears to restrict or abolish neoplastic growth and development under extreme iodine deficient conditions, where a significant level (9%) of neoplastic changes was predicted from the results of Example 3.

DIMETHYLBENZANTHRACENE STUDIES

Further confirmation of these results were obtained from a further rat model study, wherein rats which were pretreated with elemental iodine had a reduction of mean tumor volume as compared to the nontreated controls, when both of these rats were challenged with a chemical carcinogen.

After adequate orientation of 48 hours, 80 Sprague-Dawley virgin female rats (A.A.I., PA) of 100–124 grams and approximately 37 days old, were divided randomly into eight groups each containing 10 rats. The animals were identified according to their phase, group, and rat numbers. The eight groups were labelled as Groups, IA1, IA2, IB1, IB2, IIA1, IIA2, IIB1, and IIB2. Each rat was weighed and marked for identification. Ear identification were as follows:

| Group # | | Rat # |
| --- | --- | --- |
| Left Ear | | Right Ear |
| Upper hole-1 | Upper clip-4 | Upper-1 (4,7) |
| Middle hole-2 | Middle clip-5 | Middle-2 (5,8) |
| Lower hole-3 | Lower clip-6 | Lower-3 (6,9) |
| Two holes-7 | | No hole-10 |
| None-8 | | |

The rats in each group were housed in large rat cages, allowing no more than four rats per cage and 23 sq. inches floor space per rat.

Group I was initially fed a normal diet and provided with double distilled drinking water (Ionics and IWT). Group II was initially fed a Remington iodine-deficient diet (Teklad, Wi) during which they received double distilled drinking water.

At the end of fourteen days, and at 50–56 days old, groups I and II were divided into groups A and B. Groups IA and IIA were treated with 15 mg 7,12 Dimethylbenzanthracene (Eastman Kodak, N.Y.) dissolved in 1 ml sesame oil by gavage. Groups IB and IIB were given a sham feeding of 1 ml of sesame oil at this time also. Only 10 rats a day were given this treatment. For the first twelve hours after treatment, the rats were housed in the fume hood and then taken to the Animal House where they were placed in the same room as groups IB and IIB. The rats in groups IA and IIA continued to be fed a normal diet and iodine-deficient diet, respectively. Groups IB and IIB also continued to receive their respective diets.

The following phases received iodine replacement therapy at these times:

Phase 1—at time of initial feeding of Remington diet

Phase 2—at time of DMBA pulse

Phase 3—at 10 days after DMBA treatment

Groups IA1, IB1, IIA1, and IIB1 received 2.67 ml/1000 ml dilution of a 0.3 mg/ml "mother" iodine concentrate for the rest of the experiment. The technique for making the iodine solution was as follows:

1) 14 gms. prilled iodine was placed in a membrane which was sealed.

2) Membrane was placed in 1000 ml of $DDH_{20}O$ in a brown coated bottle. This was used as a concentrate.

3) The water was heated to 60° C. for 2 hours as a heat starter. It takes 24 hours to arrive at Black's Solubility Curve. This has a heat mass constant. (Stabilizes at 0.3 mg/ml)

4) A second container was used to measure 2.67 ml of concentrate to 1000 ml DD $H_2O$. This dilution was then used as drinking water for the animals.

The following was the amount of iodine given per day:

0.3 mg/ml×2.67 ml/1000 ml×25 ml/day=0.2 mg/day or 20 µg/day.

This daily dosage corresponds to the rats receiving 0.07–0.09 mg per kilogram body weight. The other groups continued to receive double distilled drinking water. Thus, the groups were arranged in the following order:

| Group | No. of rats |
| --- | --- |
| I. Normal diet | |
| A1-DMBA, iodine therapy | 10 |
| A2-DMBA, no iodine therapy | 10 |
| B1-No DMBA, iodine therapy | 10 |
| B2-No DMBA, no iodine therapy | 10 |

-continued

| Group | No. of rats |
|---|---|
| II. Iodine-deficient diet | |
| A1-DMBA, iodine therapy | 10 |
| A2-DMBA, no iodine therapy | 10 |
| B1-No DMBA, iodine therapy | 10 |
| B2-No DMBA, no iodine therapy | 10 |
| | 80 |

Starting on day one and continuing until 150 days past initial DMBA exposure, each rat was weighed once a week.

Every three weeks, vaginal smears were performed for 5 consecutive days. A report of the stage of estrous and any abnormalities were noted for each rat.

Palpations of the breasts were performed twice a week for the first 30 days after pulse DMBA was administered. The masses, if any, were drawn, measured by caliper, described as to consistency and freedom of motion, and all observations were recorded. After 30 days, the above observations were taken (including framing of tumor if larger than 5 mm) every 2 days and recorded.

Statistical analysis were performed on the results to determine the following:

A. Number of rats/group; onset and time of initial detection

B. Mammary cancers per rat at necropsy

C. Mean time to mammary cancer detection

D. Growth rate after detection as expressed as volume-doubling time when cancer reaches 1 $cm^3$ At 150 days past initial pulse dose of DMBA, groups I and II underwent $CO_2$ euthanasia. Vena cava serum, breast tissue, and thyroid tissue were collected from each rat, labelled, and analysis performed for histological data. Random weighing of adrenals, ovaries, thyroids, and breasts were employed and recorded. Cell and tissue changes under the influence of iodine were observed by light cytohistology to indicate the characteristics of breast neoplasias. The following characteristics were noted:

A) Cellular hyperplasia
B) Ductal hypertrophy
C) Fibrosis
D) Secretion

Neoplasia description will require the following observations:

A) Mean time of onset of cancer detection
B) Rate of tumor formation
C) Growth rate of tumors (doubling time)

Excision-biopsies of breast tumors were surgically removed under anesthetic whenever the greatest diameter of the rat tumor was larger than 2.5 cm, or when the appearance of the tumor resembled any stage of necrosis. If necessary, a second biopsy was taken during the chronic study, if the tumor exceeded the established maximal size, in order that the animal complete the time (150 days), which is part of the experimental design. Euthanasia was carried out if animal discomfort seemed to be present at any time.

The excision-biopsies were done under anesthesia given I.P. This anesthetic consisted of:

2 ml Ketaset (100 mg/ml)
1 ml Rompon (20 mg/ml)
0.15 ml PromAce (10 mg/ml)
Dose: 0.1 ml mix/100 g B.W.

The tumor surgery was limited to the breast and did not extend beyond the fascia. After removal, subcutaneous running absorbable sutures or skin clips were used to close the skin. Follow-up was done after surgery until vital signs recover. The rat was isolated and re-examined until the skin clips were removed and the rat could resume its activities in the original cage. When surgery appeared to be in excess of the protocol or post-op is poor, euthanasia was required.

The results of these studies are shown on Table 2. This table shows the two main groups, Group 1 and Group 2. Group 1, which was initially fed a normal diet, and Group 2 which was initially fed a Remington iodine deficient diet. Within the two groups are four subgroups, phases 1, 2 and 3, and a control. Phase 1 received iodine replacement therapy at the time of the initial feeding of either the Remington diet or the normal diet. Phase 2 received iodine replacement therapy at the time of DMBA treatment. Phase 3 received iodine replacement therapy 10 days after DMBA treatment. The controls did not receive any iodine replacement therapy.

As demonstrated from the results, pretreating the rats with iodine replacement therapy prior to DMBA treatment, reduced the mean tumor volume in the DMBA treated rats. These results quite clearly demonstrate the prophylactic capability of elemental iodine to reduce the mean tumor volume in DMBA challenged rats, thus confirming the clinical data collected thus far that women who are treated with elemental iodine have a lower incidence of breast cancer.

The dose used for treatment is in a range chosen for benign disease (that is fibrocystic disease of the breast). Since the dose that might prove toxic is 10 to 20 times this dose, modification to improve the results can be made by adjusting the dose higher.

TABLE 2

| | Mean Tumor Volume*: DMBA Treated Rats | | | | | | | |
|---|---|---|---|---|---|---|---|---|
| | Week 10 | Week 12 | Week 14 | Week 16 | Week 18 | Week 20 | Week 22 | Exp. |
| GROUP I | | | | | | | | |
| Normal Diet-Iodine Phase I | 15.191 | 53.565 | 67.739 | 97.979 | 136.405 | 155.904 | 214.962 | 320.524 |
| Normal Diet-Iodine Phase II | 7.603 | 57.853 | 106.887 | 140.751 | 216.033 | 247.025 | 320.468 | 534.001 |
| Normal Diet-Iodine Phase III | 6.686 | 24.079 | 75.421 | 90.319 | 127.529 | 184.717 | 319.229 | 392.61 |
| Normal Diet-Control | 21.744 | 33.451 | 79.839 | 148.307 | 197.307 | 264.371 | 328.232 | 461.2 |
| GROUP II | | | | | | | | |
| ID Diet-Iodine Phase I | 4.048 | 23.367 | 65.244 | 119.156 | 155.189 | 174.49 | 238.883 | 337.516 |
| ID Diet-Iodine Phase II | 0.216 | 54.934 | 111.962 | 168.475 | 269.008 | 401.774 | 519.122 | 613.044 |
| ID Diet-Iodine Phase III | 5.816 | 36.68 | 81.81 | 177.888 | 203.824 | 356.807 | 393.328 | 500.435 |
| ID Diet-Control | 25.435 | 58.454 | 123.057 | 196.918 | 231.99 | 306.082 | 389.649 | 509.238 |

*Volumes were calculated using the formula $4/3 \pi ((L + W) \div 2)$
All measurements were recorded in centimetres designating the greatest diameter the length and its corresponding greatest orthogonal diameter its width.

C. Iodine Treatment of Endometriosis

The present invention provides a method and composition for the treatment of endometriosis. Particularly, elemental iodine minimize the ovarian function and estrogen production to control endometriosis and alleviate its symptoms.

Endometriosis is characterized by hormonally responsive endometrial tissue implants in extra-uterine sites. The etiology of endometriosis is thought to be the transplantation of uterine lining cells through the fallopian tubes, the lymph channels and/or the blood stream to the abdominal cavity. Another suggested theory is that the peritoneum undergoes metaplasia to produce endometrial cells without direct access to cellular transplants. The transplanted or transformed islands of endometrial tissue act in a similar fashion to the uterine cells, with swelling and then bleeding at the time of menstruation.

Current treatment modalities for endometriosis are directed at the normal fluctuations of the estrogen/progesterone complex. Medications include birth control pills, masculinizing hormones such as danazol, or estrogen suppression drugs such as tamoxifen. In older age groups, total abdominal hysterectomy is the only therapy that is effective. All of the medical therapies are anti-estrogen.

It was found that the therapeutic treatment of human patients with an effective amount of elemental iodine ($I_2$) in a pharmaceutical carrier caused a subsidence of the nodularity of the patient's pelvic peritoneum. An effective dose of elemental iodine ($I_2$) to cause such a subsidence of nodularity is about 1 to 20 milligrams per day. A daily dosage of elemental iodine for the treatment of endometriosis of about 3 milligrams to about 6 milligrams is also useful. The daily dosage can be administered in an aqueous solution containing about 0.30 milligrams of elemental iodine per milliliter of solution.

One example of the daily dosage is based on the administration of about 0.01 to about 0.2 milligrams of elemental iodine per kilogram of patient body weight per day.

EXAMPLE 6

Treatment of Endometriosis With Iodine

In the course of treating patients with diatomic iodine for fibrocystic breast dysplasia (Example 1, above) three patients had a coincident dramatic decrease in their cyclic lower abdominal pain. Two patients (ages 17 and 15), both with a diagnosis of endometriosis and both treated with birth control pills previously with little result, were treated with diatomic iodine for 10 and 18 months, respectively. Both had a complete amelioration of their pain within one cycle of starting the medication.

As a trial, the medication was stopped in these patients, and, within one cycle, they had severe pain again, with increasing nodularity of the pelvic peritoneum on rectal examination. The subjective symptoms and physical findings again improved within one cycle of restarting diatomic iodine.

The third patient (age 36), had proven endometriosis that responded to diatomic iodine therapy within two cycles, with complete relief of pelvic pain and improvement in the pelvic nodularity on rectal examination. Upon stopping her medication, she was asymptomatic for two cycles, and then her pain returned.

This series of patients has responded to diatomic iodine, and during their trial therapy were not on any other medication. The mechanism of action of the diatomic iodine in control of endometriosis may be through the "reduction" of ovarian function and estrogen production, such as seems to be the case in the treatment of premenstrual syndrome.

D. Iodine Treatment of Premenstrual Syndrome

The present invention further relates to a method and composition for the treatment of premenstrual syndrome. Particularly, elemental iodine normalizes the ovarian function and estrogen production to alleviate the symptoms of premenstrual syndrome.

Premenstrual syndrome is defined as the cyclic recurrence in the luteal phase of the menstrual cycle of a combination of distressing physical, psychological and/or behavioral changes, of sufficient severity to result in deterioration of interpersonal relationship and/or interference with normal activities. The symptoms of premenstrual syndrome include breast pain, swelling and tenderness, lower abdominal bloating, constipation, increased appetite with cravings for salt or chocolate, fatigue, emotional lability with temper tantrums, anger or crying, depression, anxiety with tension, irritability with tendency to seek confrontations, aversion to sexual relations, insomnia, confusion and/or violence.

Although premenstrual syndrome has been classified as a psychiatric instability in the premenstrual phase, psychiatric counselling has not proven to be an effective treatment. Other treatment modalities include progesterone administration, tranquilizers and pain control medication, surgical removal of the ovaries and naloxone administration. However, these other treatment modalities are also ineffective.

It was found that an effective treatment of premenstrual syndrome in human patients entailed the administration of an effective amount of elemental iodine ($I_2$). The dose of the elemental iodine had to be sufficient to normalize the patient's ovarian function and estrogen production (both of which are abnormal in patient's with premenstrual syndrome).

An effective amount of elemental iodine ($I_2$), in a pharmaceutical carrier, to normalize the ovarian function and estrogen production is about 1.0 to about 12 milligrams per day. In one embodiment of the invention, a daily dosage of about 3 milligrams to about 6 milligrams per day was found to be effective. These doses are based on a daily dosing range of about 0.01 to about 0.20 milligrams elemental iodine ($I_2$) per kilogram of patient body weight. In one example of the invention, the daily dosage is administered as an aqueous solution containing about 0.3 milligrams of elemental iodine per milliliter of solution.

EXAMPLE 7

Treatment of Premenstrual Syndrome With Iodine

Diatomic iodine has been used for the treatment of fibrocystic disease (see Example 1, above). During this treatment, ten women not only had improvement of their breast pain, but also volunteered that their premenstrual syndrome was controlled in part or totally. This was significant because premenstrual syndrome was not discussed at their initial consultation, but each woman, at her four-month evaluation, spontaneously reported amelioration of her premenstrual syndrome within two menstrual cycles of beginning treatment. These women varied in age from 30 years to 45 years, with an average of 38 years. The dose of elemental iodine employed was from about 0.07 mg. to about 0.09 mg. per kilogram body weight per day.

In a retrospective review, the presence of their syndrome was confirmed by their family doctor, and all reported failure of control of the premenstrual syndrome with various medications. All these patients met the research diagnostic criteria for premenstrual syndrome as defined by Steiner, Haskett and Carroll. Five were classified as moderate, and five as severe. Subsequent follow up has shown continuation of control of the syndrome. Three patients stopped their medication and within one menstrual cycle had a return of symptoms.

E. Iodine Treatment of Ovarian Cysts

The present invention further relates to a method and composition for the treatment of ovarian cysts. Particularly, the elemental iodine normalizes the ovarian metabolism and estrogen response to prevent and/or treat the occurrence of ovarian cysts.

As with the other medical indications, the action of diatomic iodine in preventing or treating ovarian cysts is thought to be through a biochemical reduction of ovarian metabolism and estrogen response.

An effective amount of elemental iodine $I_2$, in a suitable pharmaceutical carrier to normalize the ovarian function and estrogen production is about 1.0 to about 12 milligrams per day. In one embodiment of the invention, a daily dosage of about 3 milligrams to about 6 milligrams per day was found to be effective. These doses are based on a daily dosing range of about 0.01 to about 0.20 milligrams elemental iodine ($I_2$) per kilogram of patient body weight. In one example of the invention, the daily dosage is administered as an aqueous solution, containing about 0.3 milligrams of elemental iodine per milliliter of solution.

EXAMPLE 8

Treatment of Ovarian Cysts with Iodine

One patient, Number 647, exemplified four of the possible effective uses of elemental iodine, i.e., for the treatment of fibrocystic breast disease, premenstrual syndrome, endometriosis, and ovarian cysts. In each situation, as previously described, the elemental iodine is acting as an anti-estrogen to normalize the ovarian metabolism and estrogen response.

A synopsis of the case follows. This patient had a previous ruptured follicle cyst of the right ovary and was referred to the private clinic for pelvic pain prior to her menarche. After menarche, the patient had recurrent episodes of right and left lower quadrant abdominal pain. An ultrasound of the pelvis, at the time of initial treatment with elemental iodine, revealed a cyst of the left ovary of approximately 1 cm in diameter. After approximately 3 months on elemental iodine, the patient was free of abdominal pain. The patient stopped taking the elemental iodine for 1 week and found that on the eighth day, her abdominal pain returned, severe enough to incapacitate her. She restarted the iodine and within 10 days the abdominal pain had subsided. A repeat ultrasound done approximately 10 months after initial treatment of iodine revealed that the cyst on her left ovary had disappeared. Approximately six months later, this patient was also diagnosed with endometriosis (presence of chocolate cysts) during a laparoscopy examination.

After a period of no abdominal pain, the patient stopped taking the elemental iodine for a period of approximately 2 years. She then returned to the private clinic, again having abdominal pain, and in addition, breast pain. She was at that time diagnosed as having fibrocystic disease in the upper half of each breast. The elemental iodine was again prescribed for her fibrocystic disease, and to continue to control her endometriosis disease, which was diagnosed on her initial laparoscopy exam. An ultrasound done approximately 6 months after elemental iodine retreatment showed the ovaries to be normal.

The patient continued on the elemental iodine, but was given an oral contraceptive as well. The patient 1 year later reported that she was free of abdominal pain. However, she stated that if she stopped the iodine medication, she developed recurrent abdominal pain within three months presumably because of ovarian cysts.

Approximately 2 years after re-treatment with elemental iodine her breasts were asymptomatic and normal on examination. She was also asymptomatic in regard to her abdomen. The patient at all times was treated with 10 ml of an aqueous solution elemental iodine, twice daily, corresponding to a dose of approximately 6 milligrams per day.

While the present invention has been described in connection with specific embodiments thereof, it will be understood that it is capable of further modifications. This disclosure of the invention is intended to cover any variations, uses or adaptations of the invention following in general, the principles of the invention, and including such departures from the present disclosure as come within known and customary practice within the art to which the invention pertains.

We claim:

1. A method for therapeutically treating or preventing an iodine deficiency disease or disorder selected from the group consisting of fibrocystic dysplasia, breast cancer, endometriosis, ovarian cysts and premenstrual syndrome, comprising administering to a mammal in need thereof a sufficient amount of elemental iodine.

2. The method of claim 1 wherein the amount of elemental iodine that is administered from about 0.01 to about 0.20 milligrams of elemental iodine per kilogram body weight per day.

3. The method of claim 2 wherein the amount of elemental iodine that is administered from about 0.03 to about 0.16 milligrams of elemental iodine per kilogram body weight per day.

4. The method of claim 1 wherein the elemental iodine is administered at a dose of from about 1 to about 20 milligrams per day.

5. The method of claim 4 wherein the elemental iodine is administered at a dose from about 2 to about 12 milligrams per day.

6. The method of claim 2, wherein elemental iodine is administered from about 0.01 to about 0.20 milligrams per kilogram body weight per day for treating fibrocystic dysplasia.

7. The method of claim 2, wherein elemental iodine is administered from about 0.01 to about 0.20 milligrams per kilogram body weight per day for treating breast cancer.

8. The method of claim 2, wherein elemental iodine is administered from about 0.01 to about 0.20 milligrams per kilogram body weight per day for preventing breast cancer.

9. The method of claim 2, wherein elemental iodine is administered from about 0.01 to about 0.20 milligrams per kilogram body weight per day for treating endometriosis.

10. The method of claim 2, wherein elemental iodine is administered from about 0.01 to about 0.20 milligrams per kilogram body weight per day for treating ovarian cysts.

11. The method of claim 2, wherein elemental iodine is administered from about 0.01 to about 0.20 milligrams per kilogram body weight per day for treating premenstrual syndrome.

* * * * *